(12) United States Patent
Filbin et al.

(10) Patent No.: US 8,673,594 B2
(45) Date of Patent: Mar. 18, 2014

(54) METHODS FOR STIMULATING NERVOUS SYSTEM REGENERATION AND REPAIR BY REGULATING ARGINASE I AND POLYAMINE SYNTHESIS

(75) Inventors: Marie T. Filbin, New York, NY (US); Rajiv R. Ratan, Cambridge, MA (US)

(73) Assignees: Research Foundation of City University of New York, New York, NY (US); Beth Israel Deaconness Medical Center, Boston, MA (US)

( * ) Notice: Subject to any disclaimer, the term of this patent is extended or adjusted under 35 U.S.C. 154(b) by 994 days.

(21) Appl. No.: 12/613,310

(22) Filed: Nov. 5, 2009

(65) Prior Publication Data

US 2010/0216710 A1 Aug. 26, 2010

Related U.S. Application Data

(62) Division of application No. 10/275,513, filed as application No. PCT/US01/14364 on May 4, 2001, now Pat. No. 7,741,310.

(60) Provisional application No. 60/202,307, filed on May 5, 2000.

(51) Int. Cl.
*C12P 21/04* (2006.01)
*C12N 5/071* (2010.01)

(52) U.S. Cl.
USPC .......................................... 435/70.1; 435/368

(58) Field of Classification Search
None
See application file for complete search history.

(56) References Cited

U.S. PATENT DOCUMENTS

| | | | |
|---|---|---|---|
| 5,395,612 A | 3/1995 | Griffith et al. | |
| 5,932,542 A | 8/1999 | Filbin | |
| 6,096,716 A * | 8/2000 | Hayes et al. | 514/44 R |
| 6,203,792 B1 | 3/2001 | Filbin | |
| 6,387,890 B1 | 5/2002 | Christianson et al. | |
| 2003/0066562 A1 | 4/2003 | Wakeman | |
| 2003/0158262 A1 | 8/2003 | Ramesh et al. | |

FOREIGN PATENT DOCUMENTS

| | | |
|---|---|---|
| WO | 9300894 A1 | 1/1993 |
| WO | 9301300 A1 | 1/1993 |
| WO | 9701352 A1 | 1/1997 |
| WO | 9711965 A1 | 4/1997 |
| WO | 9730167 A1 | 8/1997 |
| WO | 9734567 A2 | 9/1997 |
| WO | 9739629 A1 | 10/1997 |
| WO | 9739754 A1 | 10/1997 |
| WO | 9914235 A1 | 3/1999 |
| WO | 9943345 A1 | 9/1999 |
| WO | 0018799 A1 | 4/2000 |

OTHER PUBLICATIONS

Radio et al, (NeuroToxicology, 2008.29:361-376).*
Tresco et al. Advanced Drug Delivery Reviews, 2000.42:3-27).*
Bestor (J. Clin. Invest., 2000.105:409-411 ).*
Sanchez-Capelo et al (NeuroReport, 1999. 10:2169-2173).*
Salimuddin et al., "Regulation of the genes for arginase isoforms and related enzymes in mouse mactophages by lipopolysaccharide", Am J Physiol., 277:E110-E117 (1999).
Scali et al., "Brain inflammatory reaction in an animal model of neuronal degeneration and its modulation by an anti-inflammatory drug: Implication in Alzheimer's disease", The European Journal of NeuroScience, 12:1900-1912 (2000). Abstract only.
Shantz et al., "Expression of an ornithine decarboxylase dominant-negative mutant reverses eukaryotic initiation factor 4E-induced cell transformation", Cander Res., 56:5136-5140 (1996).
Shantz and Pegg et al., "Translational regulation of ornithine decarboxtlase and other enzymes of the polyamine pathway", Int. J Biochem. Cell Biol., 31:107-122 (1999).
Shantz et al., "Regulation of ornithine decarboxylase in a transformed cell line that overexpresses translation initiation factor eIF-4E", Cancer Res., 56:3265-3269 (1996).
Shantz et al., "Transcriptional and translational control of ornithine decarboxylase during Ras transformation", Biochem. J., 377:257-264 (2004).
Shaw et al., "Local delivery of interleukin 4 by retrovirus-transduced T lymphocytes amelirates experimental autoimmune encephatomyelitis", J Exp Med. 185:1711-1714 (1997).
Shi et al., "Structure of the murine arginase II gene", Mammalian Genome, 9:822-824 (1998).
Slotkin and Bartolome et al., "Role of ornithine decarboxylase and the polyamines in nervous system development:a review", Brain Res Bull., 17:307-320 (1986).

(Continued)

*Primary Examiner* — Joseph Woitach
*Assistant Examiner* — Kimberly A Aron
(74) *Attorney, Agent, or Firm* — Hoffmann & Baron, LLP

(57) ABSTRACT

This invention relates to the novel identification of arginase as an enzymatic activity which can reverse inhibition of neuronal regeneration in the central and peripheral nervous system. Assays to monitor the effects of various agents on arginase expression and thus on neuronal regeneration and repair and to identify agents which will block or promote the inhibitory effects on neuronal outgrowth are provided. This invention also relates to compositions and methods using agents that can reverse the inhibitory effects of myelin on neural regeneration by affecting arginase activity or putrescine and derivative polyamine levels in a neuron. Methods for regulating and for promoting (or repressing) neuronal growth or regeneration in the nervous system, methods for treating injuries or damage to nervous tissue or neurons, and methods for treating neural degeneration associated with conditions, disorders or diseases, comprising the step of administering at least one of the compositions according to this invention, are provided.

2 Claims, 17 Drawing Sheets

(56) References Cited

OTHER PUBLICATIONS

Tabor and Tabor et al., "Polyamines", Ann Rev Biochem., 53:749-790 (1984).
Thoenen et al., "Neurotrophins and Neuronal Plasticity", Science, 270:593-598 (1995).
Wong and Mattox et al., "The effects of polyamines and polyamine inhibitors on rat scieatic and facial nerve regeneration", Exp. Neurol., 111:263-266 (1991).
Wu and Meininger et al., "Regulation of L-arginine synthesis from L-citrulline by L-glutamine in endothelial cells", Am J Physiol. Heart Cir. Physiol., 265:H1965-H1971 (1993).
Wu and Morris Jr. et al., "Arginine metabolism: nitric oxide and beyond", Biochem J., 336:1-17 (1998).
Cai et al., "Prior exposure to neurotrophins blocks inhibition of axonal regeneration by MAG and myelin via a cAMP-dependent mechanism", Neuron, 20: 89-101; 1999.
Esch et al., "Purification of a Multipotent Antideath Activity from Bovine Liver and Its Identification as Arginase: Nitric Oxide-Independent Inhibition of Neuronal Apoptosis" J. Neurosci. 18: 4083-4095, 1998.
Mena et al., 1995. "Effects of Dibutyryl Cyclic AMP and Retinoic Acid on the Differentiation of Dopamine Neurons: Prevention of Cell Death by Dibutyryl Cyclic AMP" J. Neurochem. 65: 2612-2620.
Lucchinetti et al., "Multiple sclerosis: recent developments in neuropathology, pathogenesis, magnetic resonance imaging studies and treatment" Curr Opin Neurol. 14: 259-269 (2001).
Angeles et al., "Effects of dibutyryl cyclic AMP and retinoic acid on the differentiation of fopamine neurons: Prevention of cell death by dibutyryl cyclic AMP", Journal of Neurochemistry, 65:2612-2620 (1995).
Bach et al., 1999, "Age-related defects in spatial memory are correlated wit defects in the late phase of hippocampal long-term potentiation in vitro and are attenuated by drugs that enhance the cAMP signaling pathway", Proc. Natl Acad Sci USA, 96:5280-5285.
Baloh et al., "The GDNF family ligands and receptors—implications for neural development" Curr Opin Neurobiol. 10:103-110 (2000).
Bernstein et al., "The cellular localization of the L-ornithine decarboxylase/polyamine system in normal and diseased central nervous systems", Prog. Neurobiol., 57:485-505 (1999).
Braissant et al., "L-arginine uptake, the citrulline—No cycle and arginase II in the rat brain: an in sity hybridization study," Mol. Brain Res., 70:231-241 (1999).
Cavalli et al., "Mutagenesis of rat liver arginase expressed in *Escherichia coli*: role of conserved histidines", Biochemistry, 33:10652-10657 (1994).
Chijiwa et al., "Inhibition of Forskolin-induced neurite outgrowtrht and protein phosphorylation by a newly synthesized selective inhibitor of cyclic AMP-dependent protein kinase, N-[2[(p-bromocinnamylamino)ethyl]-5-isoquinolinesulfonamide (H-89), of PC 12D Pheochromocytoma cells", J Biol Chem, 265:5267-5272 (1990).
Chu et al., "Polyamines promote regeneration of injured axons of cultured rat hippocampal neurons," Brain Res., 673:233-241 (1995).
Cox et al., "Arginase-Boronic Acid Complex Highlights a Physiological Role in Erectile Function," Nature Struct. Biol., 6:1043-1047 (1999).
Croxford et al, "Cytokine gene therapy in experimental allergic encephalomyelitis by injection of plasmid DNA-cationic liposome complex into the central nervous system," Journal of Immunology. 160:5181-5187 (1998). (Abstract only).
Danzin et al., "Effect of alpha-difluoromethylomithine, an enzyme-activated irreversible inhibitor of ornithine decarboxylase. on polyamine levels in rat tissues," Life Sci., 24:519-524 (1979).
Das et al., "Dexamethasone and dibutyryl cyclic amp induce the expression of alpha-1 antichymotrypsin in rat astrocytes implications for Alzheimer's disease," Society for Neuroscience Abstracts, 17:1072 (1991). (Abstract only).
DeBellard et al., "Myelin-associated glycoprotein inhibits axonal regeneration from a variety of neurons via interaction with a sialoglycoprotein", Mol Cell Neurosci., 7:89-101 (1996).

Dornay et al., "Early polyamine treatment accelerates regeneration of rat sympathetic neurons", Exp. Neurol., 92:665-674 (1986).
Esch et al., "Purification of a multipotent antideath activity from bovine liver and its identification as arginase: nitric oxide-independent inhibition of neuronal apoptosis", J Neurosci., 18:4083-4095 (1998).
Ghadge et al., "Mutant superoxide dismutase-1-linked familiar amyotropic lateral sclerosis: molecular mechanisms of neuronal death and protection". J Neurosci., 17:8756-8766. (1997).
Gilad et al., "Accelerated recovery following polyamines and aminoguanidine treatment after facial nerve injury in rats", Brain Res., 724:141-144. (1996).
Gotoh and Mori et al., 1999, "Arginase II downregulates nitric oxide (NO) production and prevents NO-mediated apoptosis in murine macrophage-derived RAW 264.7 cells", J Cell Biol., 144:427-434.
Iniesta et al., "The inhibition of arginase by Nw-hydroxy-l-arginine controls the growth of *Leishmania* inside macrophages", J Exp. Med., 193:777-783 (2001).
Jelsma and Aguayo et al., "Trophic factors", Curr Opin Neurobiol., 4:717-725 (1994).
Jordan et al., "p53 expression induces apoptosis in hippocampal pyramidal neuron cultures", J. Neurosci., 17:13970-1405 (1997).
Jenkinson et al., "Comparative properties of arginases", Comp. Biochem. Physiol., 114B:107-132. (1996).
Kase et al., "K-252 compounds, novel and potent inhibitors of protein kinase C and cyclic nucleotide-dependent protein kinases," Biochem. Biophys. Res. Commun., 142:436-440 (1987).
Kauppila et al., "Polyamines enhance recovery after sciatic nerve trauma in the rat", Brain Res., 575:299-303 (1992).
Khangulov et al., "L-Arginine binding to liver arginase requires proton transfer to gateway residue His141 and coordination of the quanidinium group to the dimangenese( II, II) center", Biochemistry, 37:8539-8550. (1998).
Lindsay et al., "Neuron saving schemes", Nature, 373: 289-290 (1995).
Lindvall and Odin et al., "Clinical application of cell transplantation and neurotrophic factors in CNA disorders", Current Opinion in Neurobiology, 4:752-757 (1994).
Ma L et al., "Cyclic AMP induces functional presynaptic boutons in hippocampal CA3-CA1 neuronal cultures", Nature Neurosci., 2:24-30 (1999).
MacDonnel et al., "Nerve growth factor increases activity of ornithine decarboxylase in superior cervical ganglia of young rats", Proc Natl. Acad Sci USA, 74:4681-4684 (1977).
Martino et al., "A gene therapy approach to treat demyelinating diseases using non-replicative herpetic vectors engineered to produce cytokines", Multiple Sclerosis, 4:222-227 (1998).
Mason et al., "The GDNF Receptor: Recent Progress and Unanswered Questions", Mol Cell Neurosci., 8:112-119 (1996).
Meininger et al., "Proliferation of endothelial cells (EC) from diabetic BB rats is impared", J Vasc. Research., 33(S1):66 (262) *(1996).
Mohajeri et al., "Intramuscular grafts of myoblasts generically modified to secrete glial cell line-derived neurotrophic factor prevent motoneuron loss and disease progression in a mouse model of familial amyotrophic lateral scierosis", Human Gene Therapy, 10:1853-1866. (1999).
Montine et al., "Elevated CSF prostaglandin E2 levels in patients with probable AD", Neurology, 53:1495-1498. (1999) Abstract only.
Morris and Slotkin et al., "Beta-2 adrenergic control of ornithine decarboxylase activity in brain regions of the develping rat", J Pharmacol Exp Therapeutic., 233:141-147 (1985).
Morris et al., "Human type II arginase: sequence analysis and tissue-specific expression", Gene, 193:157-161. (1997).
Mukhopadhyay et al., "A novel role for myelin-associated glycoprotein as an inhibitor of axonal regeneration", Neuron, 13:757-767 (1994).
Nakamura et al., "Differential cellular localization of enzymes of L-arginine metabolism in the rat brain", Brain Res., 530:108-112 (1990).
Neumann and Woolf et al., "Regeneration of dorsal column fibers into and betond the lesion site following adult spinal cord injury", Neuron, 23:83-91 (1999).

(56) References Cited

OTHER PUBLICATIONS

Pelleymounter and Cullen et al., "The effects of intraseptal BDNF on cognition in rats with MS/DB lesions", Society for Neuroscience Abstracts, 18:629 (1992) Abstract only.

Perez-Navarro et al., "Intrastriatal grafting of a CDNF-producing cell line protects striatonigral neurons from quinolinic acid excitotoxicity in vivo", European Journal of Neuroscience., 11:241-249 (1999) Abstract only.

Pompl et al., "A therapeutic role for cyclooxygenase-2 inhibitors in a transgenic mouse model of amyotrophic lateral sclerosis," The FASEB Journal: Official Publ. of the Federation of American Soc. for Experimental Bio. 17:725-727 (2003) Abstract only.

Richardson and Issa et al., "Peripheral injury enhances central regeneration of primary sensory neurones", Nature. 309:791-793 (1984).

Richardson PM et al., "Axons from CNS neurons regenerate into PNS grafts" Nature 284:264-265 (1980).

Rosenblad et al., "Protection and regeneration of nigral dopaminergic neurons by neurturin or GDNF in a partial lesion model of Parkinson's disease after administration into the striatum or the lateral ventricle", European Journal of Neuroscience, 11:1554-1566 (1999). Abstract only.

Rothermel and Parker Botelho et al., "A mechanistic and kinetic analysis of the interactions of the diastereoisomers of adenosine 3', 5'-(cyclic)phosphorothioate with purified cyclic AMP-dependent protein kinase", Biochem J 251:757-762 (1988).

* cited by examiner

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Primer

```
<400> SEQUENCE: 1
gtccccaatg acagcccc                                                  18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
cttttcttcc ttcccagcag                                                20
```

METHODS FOR STIMULATING NERVOUS SYSTEM REGENERATION AND REPAIR BY REGULATING ARGINASE I AND POLYAMINE SYNTHESIS

The present application is a divisional of U.S. patent application Ser. No. 10/275,513, filed Apr. 7, 2003, which is the U.S. National Phase of International Patent Application Serial No. PCT/US01/14364, filed May 4, 2001, which claims the benefit of U.S. Provisional Patent Application Ser. No. 60/202,307, filed May 5, 2000, all of which are incorporated herein by references in their entireties.

TECHNICAL FIELD OF THE INVENTION

This invention relates to the novel identification of arginase as an enzymatic activity which can reverse inhibition of neuronal regeneration in the central and peripheral nervous system. Assays to monitor the effects of various agents on arginase expression and thus on neuronal regeneration and repair and to identify agents which will block or promote the inhibitory effects on neuronal outgrowth are provided. This invention also relates to compositions and methods using agents that can reverse the inhibitory effects of myelin on neural regeneration by affecting arginase activity or putrescine and derivative polyamine levels in a neuron. Methods for regulating and for promoting (or repressing) neuronal growth or regeneration in the nervous system, methods for treating injuries or damage to nervous tissue or neurons, and methods for treating neural degeneration associated with conditions, disorders or diseases, comprising the step of administering at least one of the compositions according to this invention, are provided.

BACKGROUND OF THE INVENTION

The adult, mammalian central nervous system (CNS) does not regenerate after injury despite the fact that there are many molecules present which promote nerve and axonal growth. The adult, mammalian peripheral nervous system (PNS), in contrast, does regenerate to some extent. It is believed that the lack of regeneration in the CNS is caused by the presence of molecules which actively prevent or inhibit regeneration. In the PNS, to the extent that neurons can regenerate, these inhibitors are thought to be removed or inactive and are thus not encountered by the re-growing axon. Hence, the well documented inability of the adult mammalian CNS to regenerate after injury is believed to result from a predominance of inhibitory molecules. There are at least three factors that are responsible for the lack of regeneration: the formation of a glial scar, inhibitors of regeneration in myelin and the intrinsic growth capacity of adult axons. The glial scar takes some time after injury to form. Therefore, it would be advantageous to encourage growth in this "window-of-opportunity", before the scar forms. The main obstacles immediately after injury, therefore, are inhibitors of neuronal regeneration present in myelin.

To overcome these inhibitors, they could either be neutralized or the growth capacity of the axon could be changed such that the axons no longer respond to myelin by being inhibited. In this way, they would resemble young axons which regenerate in vivo and which are not inhibited by myelin in vitro. Previously, we showed that if the endogenous levels of cAMP are elevated in older neurons, either artificially with dibutyryl cAMP or by pre-treating the neurons with neurotrophins ("priming"), they are not inhibited by either myelin in general or by a specific myelin inhibitor, myelin-associated glycoprotein (MAG). See Cai, D. et al., Neuron 22:89-101 (1999); see also U.S. Pat. Nos. 5,932,542 and 6,203,792, the entire disclosures of which are incorporated herein by reference. We have also shown that the endogenous level of cAMP in young neurons is very high and that their ability to regenerate in vivo and to grow on myelin is cAMP-dependent (Cai et al., supra, 2001). The drop in neuronal cAMP concentration seems to parallel the developmentally regulated switch that decreases the ability of axons to regenerate. Thus, cAMP levels may play an important role in regulating the capacity of a neuron to undergo axonal regeneration. Downstream effectors which are directly responsible for improved neuronal growth on myelin remain unknown. One candidate may be polyamines, such as spermidine and spermine, and their diamine precursor putrescine, which are ubiquitously distributed in prokaryotic and eukaryotic cells and eukaryotic tissues.

Polyamines are involved in a large number of cellular functions, including many which involve nucleic acids, such as DNA replication, gene expression and peptide synthesis. (For a review, see, e.g., Tabor and Tabor, Annu. Rev. Biochem 53, pp. 749-790 (1984)). Polyamines have been shown in some systems to be essential for cell proliferation and differentiation during wound healing. We considered it possible that, because polyamines are important in tissue wound healing, they may also function in axonal regeneration in the nervous system, which can occur with or without concomitant cell proliferation.

Polyamines are abundant in the mammalian nervous system (see, e.g., Bernstein et al., Prog. Neurobiol., 57(5), pp. 485-505 (1999)). And, polyamines have been shown to promote neurite regeneration of injured axons in cultured rat hippocampal neurons (Chu et al., Brain Res., 673, pp. 233-241 (1995)). Exogenous polyamine treatment has been reported to accelerate axonal regeneration and functional recovery of crushed peripheral (rat sciatic and facial) nerves (Dornay et al., Exp. Neurol., 92, pp. 665-674 (1986); Kauppila et al., Exp. Neurol., 99, pp. 50-58 (1988), Brain Res., 5775, pp. 299-303 (1992)). In the same peripheral nerve types, however, others have reported that exogenous polyamines had no significant effects on neural regeneration (Wong and Matto; Exp. Neurol., 111, pp. 263-266 (1991)). Polyamines appear to enhance survival of certain sympathetic neurons after axonal injury (Glad and Gilad, Brain Res., 724, pp. 141-144 (1988)). Polyamines also appear to play a role in neonatal nervous tissue development (Slotkin and Bartolome, Brain Res. Bull., 17, pp. 307-320 (1986)). Interestingly, biosynthesis of polyamines is enhanced in neurons treated with cAMP (Morris and Slotkin, J. Pharmacol. Exp. Therapeutic., 233, pp. 141-147 (1985)) or nerve growth factor (MacDonell et al, Proc. Natl. Acad. Sci. U.S.A., 74, pp. 4681-4684 (1977)). Polyamines are therefore candidates for molecules which act in a cAMP-mediated signaling pathway to regulate neural regenerative capacity in the presence of myelin inhibitors.

Polyamines in mammalian cells are synthesized from the amino acid arginine in a pathway involving at least three catalytic steps. (See FIG. 1 for a schematic diagram of polyamine synthesis). The first step in polyamine synthesis is conversion of arginine to ornithine and urea, catalyzed by the enzyme arginase. Ornithine is converted to putrescine (a diamine) by the enzyme ornithine decarboxylase (ODC), a rate-limiting enzyme in polyamine synthesis (Shantz, L. M. and Pegg, A. E., Int. J. Biochem. Cell Biol., 31(1), pp. 107-122 (1999); Wu, G. and Morris, S. M., Jr., Biochem. J., 336, pp. 1-17 (1998)). Putrescine, in turn, is the precursor to the polyamine spermidine, which can be converted to a variety of other polyamines, such as spermine (see FIG. 1).

In a number of cellular systems, ornithine decarboxylase (ODC) and arginase are co-induced (Salimuddin et al., *Am. J. Physiol.*, 277, pp. E110-117 (1999)). Thus, arginase may regulate the availability of ornithine for polyamine synthesis despite the observation that conversion of ornithine to putrescine by ODC is the rate-limiting step in polyamine synthesis. Further support for this notion comes from observations that certain cells deficient in arginase cannot proliferate unless polyamines or ornithine are provided. For example, arginase activity is severely deficient in endothelial cells of the diabetic BB rat (an animal model of human type I diabetes mellitus) (Wu and Meninger, *Am. J. Physiol. Heart Circ. Physiol.*, 265, H1965-H1971 (1993)), and these cells exhibit a marked impairment in proliferation (Meninger et al., *J. Vasc. Research*, 33 (S1): 66 (1996)). Correlations between arginase activity and polyamine synthesis also been observed in kidney and intestine. A causal relationship between arginase activity and polyamine synthesis has not, however, been established.

Arginase genes are found in bacteria, fungi, plants and animals. Two isoforms of arginase encoded by separate genes have been identified in mammalian cells (Shi et al., *Mammalian Genome*, 9, pp. 822-824 (1998); incorporated herein by reference). The two isoforms of arginase differ in molecular and immunological properties, tissue distribution, subcellular location, and regulation of expression. Type I arginase (arginase I) is a cytosolic enzyme which is highly expressed in liver and detected in only a few other tissues. Its main, but not its only, role is as a component of the urea cycle. Type II arginase (arginase II) is a mitochondrial enzyme which is expressed to varying degrees in a number of tissues but with little or no expression detectable in liver. One of the functions of arginase II is to regulate nitric oxide (NO) levels by competing with nitric oxide synthetase for arginine, the availability of which is one of the rate-limiting factors in cellular NO production (Gotoh and Mori, *J. Cell Biol.* 144, pp. 427-434 (1999)). NO, in turn, is important in the nervous system as a signaling molecule involved in cell survival, memory, and cell differentiation.

Arginase I and II are approximately 70% identical at the amino acid sequence level and differ primarily in that arginase II has a mitochondrial protein targeting sequence. (See, e.g., Morris et al., *Gene*, 193, pp. 157-161 (1997); incorporated herein by reference). A comparison of arginase sequences from the livers of rat, human, *Xenopus laevis*, yeast and *Agrobacterium* TiC58 plasmid has revealed three conserved histidine residues. At the enzymatic level, the activities of arginase I and arginase II are similar but distinguishable because arginase II is not as susceptible to feedback inhibition by ornithine as is arginase I. There is reason to believe that arginase II, like arginase I, can increase cytosolic polyamines by increasing mitochondrial ornithine, which is then transported back to the cytosol. (See Jenkinson et al., Comparative properties of arginases, *Comp. Biochem. Physiol.*, 114B, pp. 107-132 (1996)).

Arginase I and II are induced in murine macrophage cell lines by cAMP. A combination of cAMP, dexamethasone and lipopolysaccharides (LPS) leads to up-regulation of arginase I in kidney, but not in the small intestine, suggesting tissue specific regulation of arginase expression. It appears that arginase isoforms may play distinct but overlapping functional roles. To date, there is no data on the role of arginase isoforms in neuronal growth or axonal regeneration.

Recent data confirm the presence of both arginase I and arginase II in the central nervous system. In situ hybridization studies demonstrated that arginase II is distributed uniformly in the CNS in most neurons and astrocytes (Braissant et al., *Brain Res. Mol, Brain Res.*, 70, pp. 231-241 (1999)). Immunohistochemical studies have demonstrated diffuse expression of arginase I protein in the CNS (Nakamura et al., *Brain Res.*, 530, pp. 108-112 (1990)). Arginase II protein localisation data is not available.

It would be useful to be able to regulate the inhibitors of axonal regeneration in neurons for treating patients with nervous system injuries or degenerative disorders where neural regeneration is a problem. As the molecular pathways that mediate neuronal growth and regeneration have not been precisely identified, it is difficult to design effective strategies to block the action of neuronal inhibitory molecules that prevent neural regeneration. In particular, it would be useful to be able to induce or otherwise increase arginase activity in neuronal cells to test whether such induction can—alone or in combination with other molecules—relieve inhibition of axonal outgrowth by myelin and myelin inhibitors, such as myelin-associated glycoprotein (MAG).

SUMMARY OF THE INVENTION

The present invention solves the problems referred to above by identifying arginase as an enzyme whose activity can reverse inhibition by myelin of neural regeneration in the central and peripheral nervous system. We demonstrate that cAMP induces arginase polynucleotide and polypeptides levels in neurons. We also identify a physiological role for arginase in the central nervous system (CNS) by showing for the first time that arginase expression is necessary and sufficient for neurite outgrowth in the presence of glial inhibitors. We also demonstrate that arginase over-expression in nerve cells is sufficient to increase polyamines to levels which relieve inhibition of neuronal regeneration by myelin and myelin inhibitors such as MAG.

The present invention provides a composition comprising an agent which Can overcome myelin-dependent growth regulation of a neuron by affecting the endogenous levels of polyamines (such as spermidine or spermine, or the precursor putrescine) in the neuron. In one embodiment, the agent increases polyamines in a particular neuron at a particular developmental stage to a level which overcomes myelin-dependent growth regulation. In another embodiment, the agent decreases polyamines in a particular neuron at a particular developmental stage to a level which overcomes myelin-dependent growth regulation. In preferred embodiments, the agent affects the endogenous level of putrescine and putrescine-derived polyamines in a neuron.

The present invention also provides a composition comprising an arginase modulatory agent which increases the biological activity of arginase in a neuron (i.e., is a neuronal arginase agonist), in an amount effective for altering neuronal growth or regeneration. In one embodiment, the arginase agonist comprises a nucleic acid molecule which, upon expression in a neuron, can increase the biological activity of arginase. Preferably, the agent comprises a nucleic acid molecule which encodes arginase, or muteins, analogs, fusions or fragments thereof, having arginase biological activity in a neuron. In another preferred embodiment, the agent comprises a non-arginase encoding nucleic acid molecule which, upon expression, increases the arginase biological activity in a neuron. In another embodiment, the arginase agonist is a protein or small molecule which increases the arginase biological activity in a neuron. In a preferred embodiment, the arginase agonist is selected from the group consisting of TGFβ, IL4, IL10 and PGE2. In another embodiment, the agent comprises a trophic factor. Preferably, the trophic factor is selected from the group consisting of a neurotrophin, EGF, PDGF, bFGF, neuroregulin (also known as aria, GGF or neu), oncostatin M and LIFT. In a preferred embodiment, the trophic factor is a neurotrophin selected from the group consisting of BDNF, GDNF, NGF, NT3, NT4 (NT4/5), IGF1, CNTF and galanin. More preferably, the neurotrophin is selected from the group consisting of BDNF, GDNF, NGF, NT3 and NT4 (NT4/5), and most preferably, is BDNF or GDNF. In another embodiment, the arginase agonist is a substance which increases cAMP levels in a neuron. Preferably, the substance is a non-hydrolyzable cAMP analog, such as dibutyryl cAMP or Sp-cAMP.

The present invention also provides a composition comprising an arginase modulatory agent which decreases the biological activity of arginase in a neuron (i.e., a neuronal arginase antagonist) in an amount effective for altering neural growth or regeneration. In one embodiment, the agent comprises a nucleic acid molecule which, upon expression in a neuron, can decrease the biological activity of arginase. In a preferred embodiment, the agent comprises a nucleic acid molecule which encodes an arginase antagonist, such as an antisense RNA or other hybrid nucleic acid, or a mutein, analog, fusion or fragment of arginase that inhibits endogenous arginase biological activity in a neuron. In another preferred embodiment, the agent comprises a non-arginase encoding nucleic acid molecule which, upon expression, decreases the arginase biological activity in a neuron. In another preferred embodiment, the arginase antagonist is a protein or small molecule which decreases the arginase biological activity in a neuron, such as a protein kinase A inhibitor.

The present invention also provides a method for relieving (in part or in full) inhibition by myelin or MAG of neuronal growth or regeneration by altering endogenous polyamine levels; and a method for relieving (in part or in full) inhibition by myelin or MAG of neuronal growth or regeneration by altering arginase bioactivity in a neuron, each comprising the step of administering, in a manner which can affect the nervous system, a composition of the invention. Methods for regulating neural growth or regeneration in the nervous system; methods for treating injuries or damage to nervous tissue or neurons; methods for treating neural degeneration associated with disorders or diseases; and methods for treating a disease, disorder or condition associated with apoptosis, necrosis or other forms of cell death; which comprise the step of administering, in a manner which can affect the nervous system, a composition of the invention, are also provided. Optionally, each of the methods further comprises the step of monitoring the growth of a neuron after the step of administering the composition.

The present invention provides an assay for determining whether neurite outgrowth from a particular type of neuron at a particular age is stimulated or inhibited in the presence of myelin or MAG and an arginase modulatory agent. In one embodiment, the method comprises the steps of:

a) culturing a first sample of a selected neuronal cell type on a growth-permissive substrate comprising purified myelin;

b) culturing a second sample of the selected neuronal cell type on a growth-permissive substrate comprising purified myelin and at least one added arginase modulatory agent; and c) comparing the relative amount of neurite growth in the cultured cells of a) and b);

wherein when the relative growth of neurites in the cultured cells of b) is greater than in a), neurite outgrowth from the selected neuronal cell type is stimulated by the arginase modulatory agent in the presence of myelin; and when the relative growth of neurites in the cultured cells of b) is less than in a), neurite outgrowth from the selected neuronal cell type is inhibited by the arginase modulatory agent in the presence of myelin. The one or more arginase modulatory agents may be added before, after, or simultaneously with addition of myelin to the selected neuronal cells. Preferably the myelin is myelin purified from the central nervous system (CNS).

In another embodiment, the method comprises the steps of:

a) culturing a first sample of a selected neuronal cell type on a growth-permissive substrate comprising MAG;

b) culturing a second sample of the selected neuronal cell type on a growth-permissive substrate comprising MAG and at least one added arginase modulatory agent; and c) comparing the relative amount of neurite growth in the cultured cells of a) and b);

wherein when the relative growth of neurites in the cultured cells of b) is greater than in a), neurite outgrowth from the selected neuronal cell type is stimulated by the arginase modulatory agent in the presence of MAG; and when the relative growth of neurites in the cultured cells of b) is less than in a), neurite outgrowth from the selected neuronal cell type is inhibited by the arginase modulatory agent in the presence of MAG. The one or more arginase modulatory agents may be added before, after, or simultaneously with addition of MAG to the selected neuronal cells.

In one preferred embodiment, the growth-permissive substrate comprising MAG is a surface comprising bound MAG molecules. More preferably, the surface is a cell engineered to produce cell surface MAG. In another preferred embodiment, the growth-permissive substrate comprises soluble forms of MAG.

DETAILED DESCRIPTION OF THE INVENTION

Figure 1:
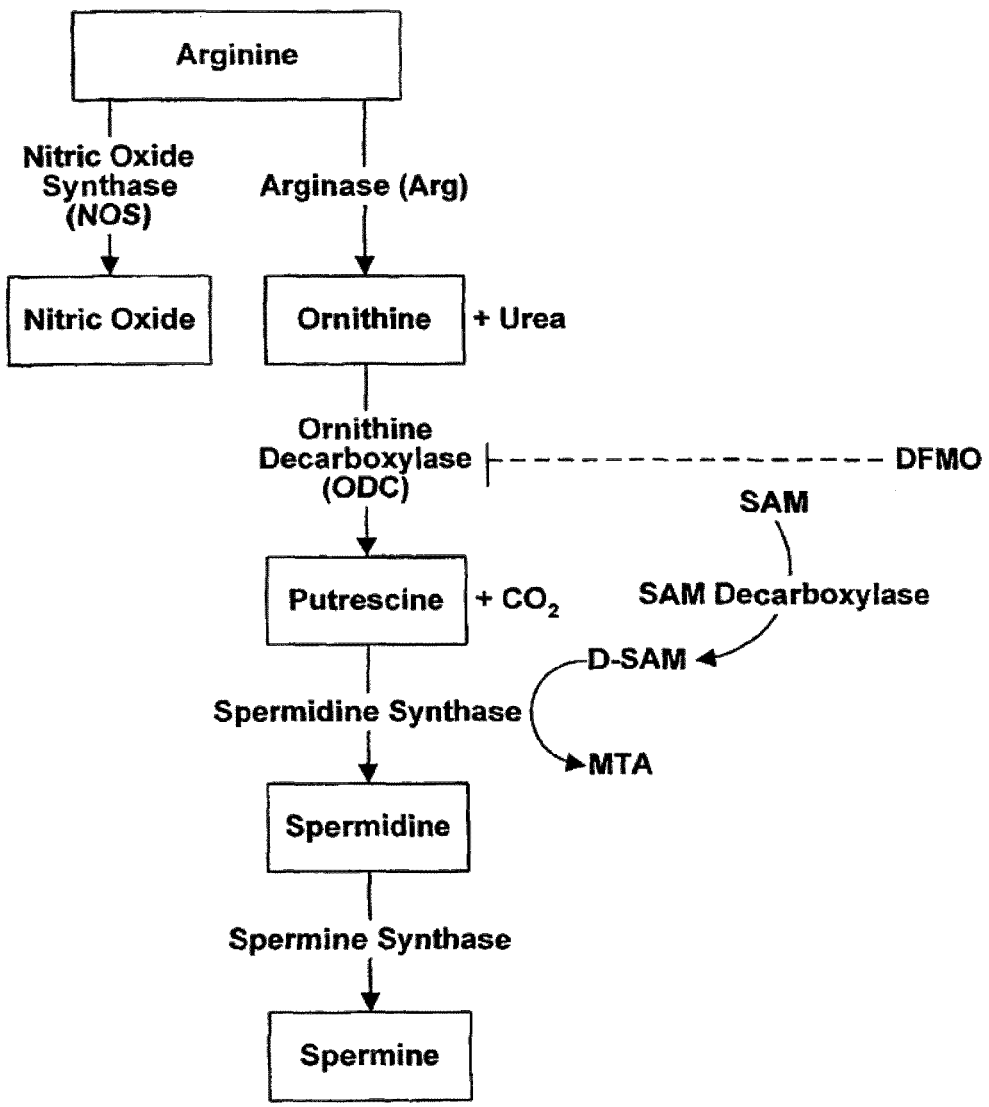
FIG. 1: Biosynthesis of Polyamines—Schematic

In order that the invention herein described may be fully understood, the following detailed description is set forth.

DEFINITIONS AND GENERAL TECHNIQUES

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of cell and tissue culture, molecular biology, immunology, neurobiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Ausubel et al., Current Protocols in Molecular Biology, Greene Publishing Associates (1992 and Supplements to 2001); Crawley et al., Current Protocols in Neuroscience, John Wiley and Sons (1997 and supplements to 2001); Kleitman et al., Culturing Nerve Cells, pp. 337-78, MIT-Press, Cambridge, Mass./London, England (G. Banker and K. Goslin, Eds.) (1991); Harlow and Lane Antibodies: A Laboratory Manual Cold Spring Harbor Laboratory Press, Cold Spring Harbor, N.Y. (1990); and Sambrook et al., Molecular Cloning: A Laboratory Manual, 2d ed., Cold Spring Harbor Laboratory Press, Cold Spring Harbor, N.Y. (1989); each of which is incorporated herein by reference in its entirety.

Enzymatic reactions and cell culture and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "arginase" refers to an enzyme that is capable of catalyzing conversion of the amino acid arginine (arg) to ornithine. Such conversion may be assessed by any of a number of methods well known to those of skill in the art, including enzymatic assays using a labeled or otherwise detectable substrate. In a preferred embodiment, an arginase is derived from a mammalian cell, e.g., rat, mouse, bovine or human. In a more preferred embodiment, an arginase is derived by expression of a polynucleotide derived from a mammalian cell, e.g., rat, mouse, bovine or human, such as from: a) the human ArgI liver polynucleotide sequence (GenBank Accession No. NM 000045 and references cited therein, all of which are incorporated herein by reference); b) the human ArgII polynucleotide sequence (GenBank Accession No. NM 001172 and references cited therein, all of which are incorporated herein by reference); or c) from an arginase polynucleotide sequence that hybridizes under stringent conditions to a) or b). In an even more preferred embodiment, the arginase is derived by expression of a polynucleotide derived from a mammalian neuron or glial cell.

The term "arginase activity" refers to an enzymatic activity of an arginase, or a mutein, homologous protein, analog, derivative, fusion or fragment thereof; that catalyzes the conversion of arginine (arg) to ornithine. Arginase enzymatic assays are well known to those of skill in the art. In a preferred embodiment, a characteristic of arginase activity, e.g., association and dissociation constants, catalytic rates and substrate turnover rates, is the same as that characteristic possessed by the arginase expressed from the human ArgI liver polynucleotide sequence (GenBank Accession No. NM 000045 and references cited therein). In another preferred embodiment, the arginase activity is different from that of an arginase expressed from the human ArgI liver polynucleotide sequence (GenBank Accession No. NM 000045 and references cited therein). An arginase activity that is different may be one, e.g., that has an increase or decrease in catalytic activity or that has a different association and/or dissociation constant compared to that of an arginase expressed from the human ArgI liver polynucleotide sequence (GenBank Accession No. NM 000045 and references cited therein).

An agent which alters or modulates the arginase "activity", "bioactivity" or "biological activity" in a neuron refers to an agent which can directly or ultimately increase (agonist) or decrease (antagonist) arginase enzymatic activity (the conversion of arginine to ornithine), or the immediately measurable results of such activity (e.g., increased ornithine and derivative polyamine synthesis) in a neuron. Arginase activity may be modulated by altering levels of DNA, RNA or protein encoding arginase or an arginase modulatory agent in a neuron. Arginase activity may also be modulated by mutation or alteration of an arginase polynucleotide or polypeptide molecule directly. Such mutations or alterations include, but are not limited to, those which alter a substrate affinity constant or binding rate, a substrate dissociation rate, the catalytic or turnover rate of the enzyme, and the binding constant of an arginase subunit to another homologous or heterologous subunit or molecule which affects (increases or decreases) catalysis by the arginase molecule. Arginase activity in a neuron may also be modulated by association (covalent or non-covalent) with another agent or factor.

Arginase activity may be measured directly by arginase specific enzymatic assays (infra) or indirectly by assaying arginase encoding nucleic acid levels in a cell (e.g., by RT-PCR, Northern blot analysis or other methods for measuring levels of steady-state RNA encoding arginase), or arginase specific protein molecules in a cell (e.g., by a variety of immunoaffinity procedures, including Western blot techniques, ELISA assays and the like)—all of which are techniques that are well-known to those of skill in the art and which are described herein.

The arginase activity to be modulated according to the invention may be expressed from a wild-type (endogenous or exogenous) polynucleotide or polypeptide encoding arginase. The activity may also be expressed from a modified polynucleotide or protein encoding arginase, including but not limited to muteins, analogs, fusions or fragments thereof having arginase biological activity in a neuron.

The terms "axonal growth" or "axonal regeneration" as used herein refer both to the ability of an axon to grow and to the ability of an axon to sprout. An axon sprout is defined as a new process that extends from an existing or growing axon (See, e.g., Ma et al., *Nat. Neurosci.*, 2, pp. 24-30 (1999), which is incorporated herein by reference).

The term "MAG" refers to myelin-associated glycoprotein, which is a molecule derived from myelin which promotes or inhibits neuronal growth and regeneration in the CNS and PNS depending on the cell type and the developmental stage of the neuron. The term "MAG" also refers to a "MAG derivative", which is a molecule comprising at least one MAG extracellular domain, wherein the MAG molecule has been altered (e.g., by recombinant DNA techniques to make chimera with portions of other molecules fused to the MAG molecule, or by chemical or enzymatic modification) or mutated (e.g., internal deletions, insertions, rearrangements and point mutations). MAG derivatives, unless otherwise noted, retain MAG activity.

The terms "MAG bioactivity" and "MAG biological activity" refer to the ability of a molecule, especially an altered or mutant form of MAG, to inhibit or promote neurite outgrowth of a selected neuronal cell type of a particular age, as detected in a neurite outgrowth assay such as those described herein, in qualitatively the same direction as cell-surface or soluble MAG. The term "MAG binding activity" refers to the ability of a molecule, especially an altered or mutant form of MAG, to compete with cell-surface MAG or soluble MAG for sialic-acid dependent neuron binding in an assay such as those described herein. For example, preferred inhibitors of MAG retain MAG binding activity but have reduced or absent MAG bioactivity. The term "MAG activity" refers generically to MAG bioactivity and binding activity as described above.

The term "polynucleotide" or "nucleic acid molecule" refers to a polymeric form of nucleotides of at least 15 bases in length, either ribonucleotides or deoxynucleotides or a modified form of either type of nucleotide. The term includes single- and double-stranded forms of DNA and RNA, and sense or antisense orientations with respect to coding sequences. In addition, a polynucleotide may include either or both naturally-occurring and modified nucleotides linked together by naturally-occurring and/or non-naturally occurring nucleotide linkages.

The term "naturally-occurring nucleotide" referred to herein includes naturally-occurring deoxyribonucleotides and ribonucleotides. The term "modified nucleotides" referred to herein includes nucleotides with modified or substituted sugar groups and the like. The term "nucleotide linkages" referred to herein includes nucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. Nucl. Acids Res. 14:9081 (1986); Stec et al. J. Am. Chem. Soc. 106:6077 (1984); Stein et al. Nucl. Acids Res. 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemica Reviews 90:543 (1990), the disclosures of which are hereby incorporated by reference.

The term "allelic variant" refers to one of two or more alternative naturally-occurring forms of a gene, wherein each gene possesses a unique nucleotide sequence. In a preferred embodiment, different alleles of a given gene have similar or identical biological properties.

Unless specified otherwise, the left hand end of a polynucleotide sequence in sense orientation is the 5' end and the right hand end of the sequence is the 3' end. In addition, the left hand direction of a polynucleotide sequence in sense orientation is referred to as the 5' direction, while the right hand direction of the polynucleotide sequence is referred to as the 3' direction.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least 30 about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, BLAST, Gap or Bestfit, which are software programs in Wisconsin Package Version 10.0, Genetics Computer Group (GCG), Madison, Wis. PASTA provides alignments and percent sequence identity of the regions of the best overlap between the query and search sequences (Pearson, 1990, herein incorporated by reference). For definitional purposes, percent sequence identity between nucleic acid sequences can be determined using PASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 55%, more preferably 60% of the nucleotide bases, usually at least about 70%, more usually at least about 80%, preferably at least about 90%, and more preferably at least about 95-98% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity—preferably at least about 65%, more preferably at least about 75%, and most preferably at least about 90%—over a stretch of at least about 14 nucleotides. See, e.g., Kanehisa, *Nucleic Acids Res.,* 12, pp. 203-13, (1984), incorporated herein by reference.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., supra, page 9.51, hereby incorporated by reference.

The Tm for a particular DNA-DNA hybrid can be estimated by the formula:

$$Tm=81.5° C.+16.6(\log 10[Na+])+0.41(\text{fraction } G+C)-0.63(\% \text{ formamide})-(600/l) \text{ where l is the length of the hybrid in base pairs.}$$

The Tm for a particular RNA-RNA hybrid can be estimated by the formula:

$$Tm=79.8° C.+18.5(\log 10[Na+])+0.58(\text{fraction } G+C)+11.8(\text{fraction } G+C)2-0.35(\% \text{ formamide})-(820/l).$$

The Tm for a particular RNA DNA hybrid can be estimated by the formula:

$$Tm = 79.8°\text{C} + 18.5(\log 10[Na+]) + 0.58(\text{fraction } G+C) + 11.8(\text{fraction } G+C)2 - 0.50(\% \text{ formamide}) - (820/l).$$

In general, the Tm decreases by 1-1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10-15° C. would be subtracted from the calculated Tm of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well known in the art.

As defined herein, stringent hybridization conditions for hybridization of complementary nucleic acid sequences having more than 100 complementary residues on a filter in a Southern or Northern blot or for screening a library is 50% formamide/6×SSC at 42° C. for at least ten hours. Hybridization buffers may also include blocking agents to lower background. These agents are well-known in the art. See Sambrook et al., supra, pages 8.46 and 9.46-9.58, herein incorporated by reference.

As appreciated by those of skill in the art, wash conditions can also be altered to change stringency conditions. As defined herein, a stringent wash condition for duplex DNA of more than 100 base pairs is a 0.2×SSC wash at 65° C. for 15 minutes (see Sambrook et al., supra, for SSC buffer). The high stringency wash is preferably preceded by a low stringency wash for such a duplex (4×SSC at 40° C. for 15 minutes) to remove excess probe. In general, signal-to-noise ratio of 2× or higher than that observed for an unrelated probe in the particular hybridization assay indicates detection of a specific hybridization.

As defined herein, nucleic acids that do not hybridize to each other under stringent conditions are still substantially homologous to one another if they encode polypeptides that are substantially identical to each other. This occurs, for example, when a nucleic acid is created synthetically or recombinantly using a high codon degeneracy as permitted by the redundancy of the genetic code.

The arginase encoding polynucleotides of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels (e.g., fluorescent, photometric, radioactive or immunological tags), methylation, phosphorylation, biotinylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. In a preferred embodiment, the nucleic acid sequence is the wild type nucleic acid sequence for arginase. The nucleic acid sequence may be mutated by any method known in the art.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect transcription into RNA, and, where appropriate, the expression of protein coding sequences, from polynucleotide sequences to which the expression control sequences are operatively linked. Expression control sequences Ware sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the genome of a virus that infects a particular host cell of interest. Many viral vectors have been developed for gene transfer into mammalian cells. Often the viral genome has been modified to delete viral genes that are not essential for infection or subsequent replication of the virus and expression of genes in an appropriate host cell. Some host cells have been engineered to express gene products necessary for viral vector replication and expression. Certain vectors are capable of autonomous replication in a host cell into which they are introduced (e.g., bacterial vectors having a bacterial origin of replication). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "polypeptide" encompasses both naturally-occurring and non-naturally-occurring proteins and polypeptides, polypeptide fragments, fusions, mutants, derivatives and analogs. A polypeptide may be monomeric or polymeric.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, fluorescent moieties or biotin, and various enzymatic modifications, as will be readily appreciated by those well skilled in the art. A variety of methods for labeling polypeptides and of substituents or labels useful for such purposes are well known in the art, and include radioactive isotopes such as 125I, 32P, 35S, and 3H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., 1992, hereby incorporated by reference.

The term "fusion protein" refers to polypeptides comprising polypeptides or fragments coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "analog" refers to both polypeptide analogs and non-peptide analogs. The term "polypeptide analog" as used herein refers to a polypeptide that is comprised of a segment of at least 25 amino acids that has substantial identity to a portion of an amino acid sequence and that has enzyme activity. Typically, polypeptide analogs comprise a conservative amino acid substitution (or insertion or deletion) with respect to the naturally-occurring sequence. Analogs typically are at least 20 amino acids long, preferably at least 50 amino acids long or longer, and can often be as long as a full-length naturally-occurring polypeptide.

The term "non-peptide analog" refers to a compound with properties that are analogous to those of a reference polypeptide. A non-peptide compound may also be termed a "peptide mimetic" or a "peptidomimetic." See, e.g., Fauchere, *J. Adv. Drug Res.* 15:29 (1986); Veber and Freidinger, *TINS p.* 392 (1985); and Evans et al., *J. Med. Chem.* 30:1229 (1987), which are incorporated herein by reference. Such compounds are often developed with the aid of computerized molecular modeling. Peptide mimetics that are structurally similar to useful peptides may be used to Produce an equivalent effect. Generally, peptidomimetics are structurally similar to a paradigm polypeptide (i.e., a polypeptide that has a desired biochemical property or pharmacological activity), such as an arginase, but have one or more peptide linkages optionally replaced by a linkage selected from the group consisting of —CH2NH—, —CH2S—, —CH2-CH2-, —CH=CH—(cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, *Ann. Rev. Biochem.*, 61:387 (1992), incorporated herein by reference); for example, by adding internal cysteine residues capable of forming intramolecular disulfide bridges which cyclize the peptide.

A "polypeptide mutant" or "mutein" refers to a polypeptide whose sequence contains substitutions, insertions or deletions of one or more amino acids compared to the amino acid sequence of a native or wild type protein A mutein may have one or more amino acid point substitutions, in which a single amino acid at a position has been changed to another amino acid, one or more insertions and/or deletions, in which one or more amino acids are inserted or deleted, respectively; in the sequence of the naturally-occurring protein, and/or truncations of the amino acid sequence at either or both the amino or carboxy termini. Further, a mutein may have the same or different biological activity as the naturally-occurring protein. For instance, a mutein may have an increased or decreased biological activity. In a preferred embodiment of the present invention, a mutein has the same or increased arginase activity as a naturally-occurring arginase. A mutein has at least 50% sequence homology to the wild type protein, preferred is 60% sequence homology, more preferred is 70% sequence homology. Even more preferred are muteins having 80%, 85% or 90% sequence homology to the wild type protein. In an even more preferred embodiment, a mutein exhibits 95% sequence identity, even more preferably 97%, even more preferably 98% and even more preferably 99%. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing New York, N.Y. (1991)); and Thornton et al. Nature 354:105 (1991), which are each incorporated herein by reference.

As used herein, the twenty conventional amino acids and their abbreviations follow conventional usage. See Immunology—A Synthesis (2nd Edition, E. S. Golub and DR Gren, Eds., Sinauer Associates, Sunderland, Mass. (1991)), which is incorporated herein by reference.

A protein has "homology" or is "homologous" to a protein from another organism if the encoded amino acid sequence of the protein has a similar sequence to the encoded amino acid sequence of a protein of a different organism. Alternatively, a protein may have homology or be homologous to another protein if the two proteins have similar amino acid sequences. Although two proteins are said to be "homologous," this does not imply that there is necessarily an evolutionary relationship between the proteins. Instead, the term "homologous" is defined to mean that the two proteins have similar amino acid sequences. In a preferred embodiment, a homologous protein is one that exhibits at least 55% sequence identity to the naturally occurring, reference protein, preferred is 60% sequence identity, more preferred is 70% sequence identity. Even more preferred are homologous proteins that exhibit 80%, 85% or 90% sequence identity to the reference protein. In a yet more preferred embodiment, a homologous protein exhibits 95%, 97%, 98% or 99% sequence identity. In addition, although in many cases proteins with similar amino acid sequences will have similar functions, the term "homologous" does not imply that the proteins must be functionally similar to each other.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for mating this adjustment are well known to those of skill in the art (see; e.g., Pearson et al., 1994, herein incorporated by reference).

The following six groups each contain amino acids that are conservative substitutions for one another:
1) Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Alanine (A), Valine (V), and
6) Phenylalanine (F), Tyrosine (Y), Tryptophan (W).

Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "BLASTP", "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

Database searching using amino acid sequences can be measured by algorithms such as BLASTP known in the art. For definitional purposes of percent sequence identity between amino acid sequences, polypeptide sequences are preferably compared using FASTA with its default parameters (a word size of 2 and the PAM250 scoring matrix), as provided in GCG Version 6.1, herein incorporated by reference. FASTA provides alignments and percent sequence identity of the regions of the best overlap between the query and search sequences (Pearson, 1990, herein incorporated by reference).

The term "neurotrophin" refers to a trophic factor that helps a neuron survive or grow. A neurotrophin elevates cyclic AMP (cAMP) levels in a neuron.

The term "patient" includes human and veterinary subjects.

The term "putrescine-derived polyamine" refers to a polyamine made in a cell from a putrescine molecule or a molecule that was derived from a putrescine molecule. The putrescine molecule can be one that is made in the host cell or one that is transported into the host cell.

A "trophic factor" is a substance that helps a cell survive or grow and which elevates cyclic AMP (cAMP) levels.

A non-hydrolyzable cyclic AMP (cAMP) analog is a cAMP having a phosphodiesterase-resistant linkage and which therefore has greater bioactivity than an unmodified cAMP molecule. Examples include dibutyryl cAMP (db-cAMP) (Posternak and Weimann, *Methods Enzymol.*, 38, pp. 399-409 (1974); incorporated herein by reference); and Sp-cAMP (Dostmann et al., *J. Biol. Chem.*, 265, pp. 10484-491 (1990); incorporated herein by reference).

Throughout this specification and claims, the word "comprise," or variations such as "comprises" or "comprising," will be understood to imply the inclusion of a stated integer or group of integers but not the exclusion of any other integer or group of integers.

Cyclic AMP-Induced Axonal Growth on MAG or Myelin is Transcription Dependent

Figure 2A:
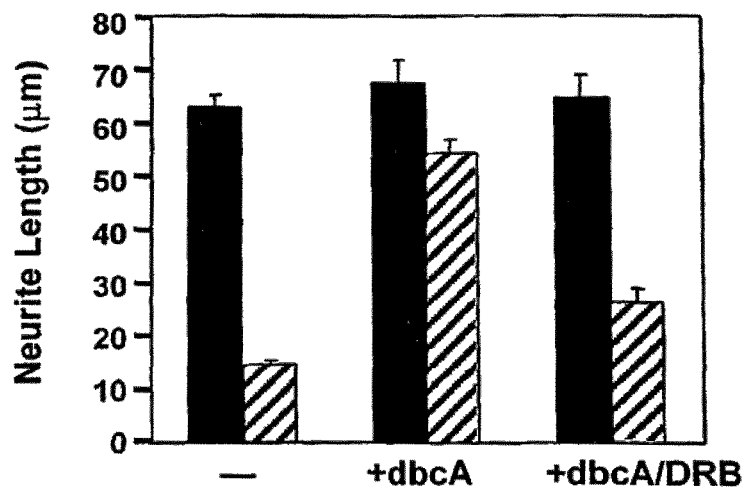
FIG. 2: Improved Axonal Growth on MAG Induced By Elevating cAMP Levels is Transcription-Dependent. (A) Isolated cerebellar neurons at a density of 20,000 neurons per well were plated onto a monolayer of either MAG-expressing Chinese hamster ovary (CHO) cells (striped bars) or control CHO cells (black bars) and cultured overnight before being fixed and immunostained for GAP43 to visualize the neurites. The length of the longest neurite per neuron, from 180-200 neurons, was measured and results are the average length+/−SEM. Where indicated, dibutyryl cAMP (dbcA) at 1 mM in the presence or absence of the inhibitor of transcription, 5,6-dichloro-1-b-D-ribofuranosylbenzimidazole (DRB) at 5 µM, was added to each culture. (B) Cerebellar neurons ($1\times10^6$) were plated onto poly-L-lysine and cultured overnight with brain-derived neurotrophic factor (BDNF) at 200 ng/ml, (termed priming) in the presence or absence of DRB at 5 µM, before being transferred to the CHO cell monolayers.
Figure 2B:
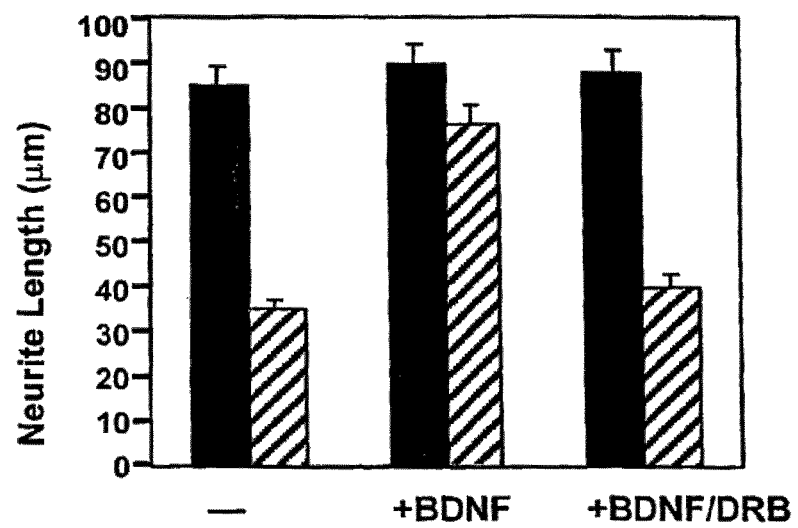

To determine whether the cAMP-induced relief of axonal outgrowth inhibition by MAG or myelin depends on transcription, we added a transcriptional inhibitor (5,6-dichloro-1-b-D-ribofuranosylbenzimidazole or "DRB") to neuronal cultures in which cAMP levels had been increased (see Example 1). As shown in FIG. 2, elevating cAMP levels in neurons, either by (A) adding dibutyryl (db) cAMP directly to neurons growing on MAG-expressing or control cells; or (B) by priming with neurotrophins (BDNF), blocks inhibition of neuronal growth by MAG. However, if the transcriptional inhibitor DRB is included in the cultures, neither dbcAMP nor BDNF block inhibition; MAG still inhibits axonal growth. Thus, the ability of dbcAMP and BDNF to block MAG-dependent inhibition of neurite outgrowth depends on the production of one or more RNAs, and presumably, expression of encoded proteins.

Figure 3A:
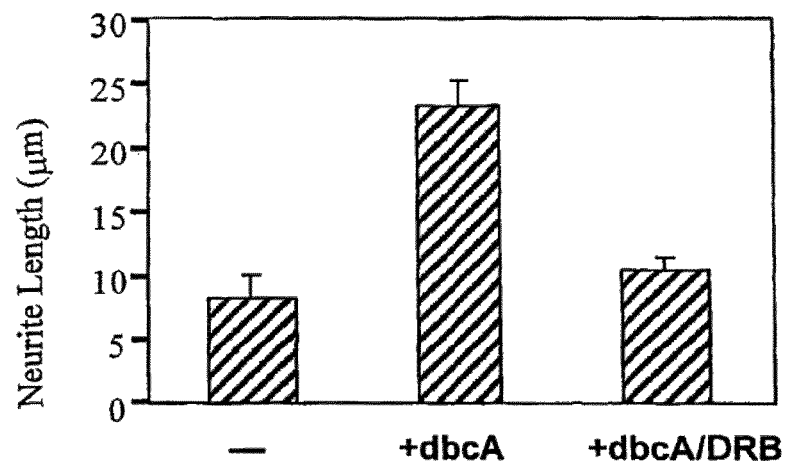
FIG. 3: Improved Axonal Growth on Myelin Induced By Elevating cAMP Levels is Transcription-Dependent. (A). Isolated cerebellar neurons at a density of 20,000 neurons per well were plated onto a substrate of purified CNS myelin and cultured overnight before being fixed and immunostained for GAP43. The length of the longest neurite per neuron from 180-200 neurons was measured and results are the average length+/−SEM. Where indicated, dibutyryl cAMP (dbcA) at 1 mM in the presence or absence of the inhibitor of transcription, 5,6-dichloro-1-b-D-ribofuranosylbenzimidazole (DRB) at 5 µM, was added to each culture. (B) Cerebellar neurons ($1\times10^6$) were plated onto poly-L-lysine and cultured overnight with brain-derived neurotrophic factor (BDNF) at 200 ng/ml, (termed priming) in the presence or absence of DRB at 5 µM, before being transferred to the CNS myelin substrate.
Figure 3B:
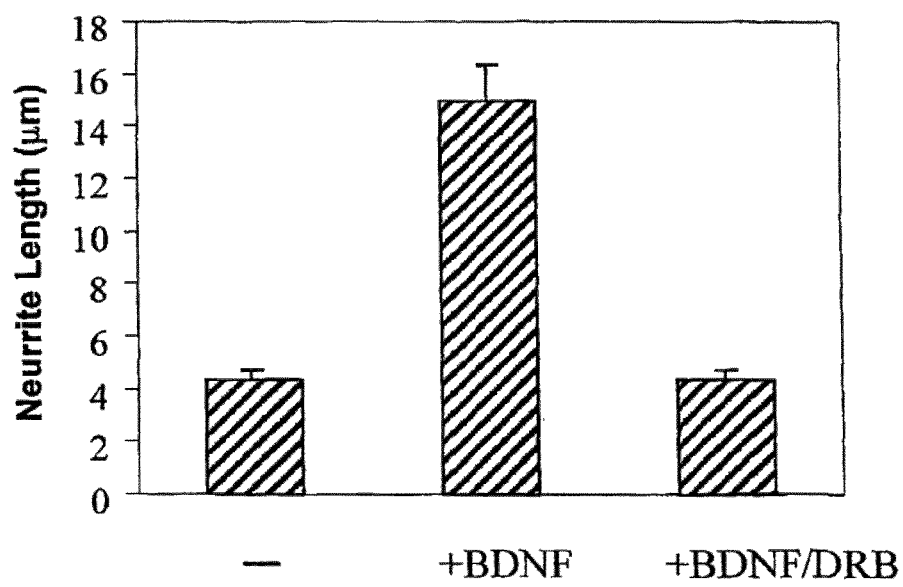

When similar experiments were carried out using purified CNS myelin as a substrate rather than MAG-expressing CHO cells (Example 1), similar results were obtained (FIG. 3). The block of myelin-dependent inhibition mediated by elevating cAMP levels (by treatment with dbcAMP or by priming with BDNF) is completely lost in the presence of a transcriptional inhibitor.

Arginase is Up-Regulated when cAMP Levels are Elevated

We next wanted to determine which target genes are up-regulated by elevated cAMP following dbcAMP treatment or neurotrophin (e.g., BDNF and GDNF) priming. If the synthesis of polyamines is important in the cAMP-induced block of inhibition by MAG and myelin, it seemed possible that expression levels of one or more of the polyamine biosynthetic enzymes would be coordinately up-regulated. Arginase (Arg), ornithine decarboxylase (ODC) and S-adenosylmethionine decarboxylase (SAM) are the first three enzymes involved in polyamine production (FIG. 1): Arginase is a cytosolic enzyme which converts arginine to ornithine and urea. A rate limiting step in poly mine synthesis is the subsequent conversion of ornithine to putrescine and $CO_2$ by ornithine decarboxylase (ODC). Putrescine can then be converted to other polyamines ("putrescine-derived polyamines") (FIG. 1; see also Slotkin and Bartolome, 1986).

To determine whether elevated cAMP levels causes an up-regulation of arginase expression, cerebellar neurons were primed with neurotrophins (BDNF) or dbcAMP (Example 1), and RNA and protein was extracted from primed neurons (Example 2). The extracted RNA was used as a template for reverse transcription and PCR amplification using primers specific for the gene encoding the enzyme arginase I ("Arg I"), an isoform of arginase abundant in liver tissue but barely detectable in other tissues. The results of the amplification are shown in FIG. 4.

Figure 4A:
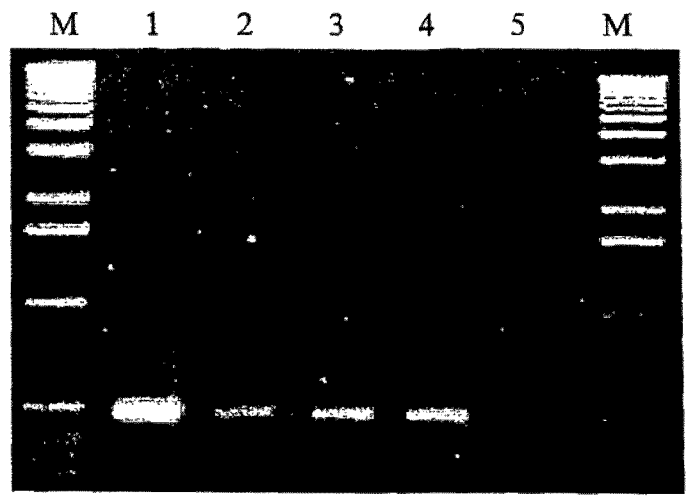
FIG. 4: Priming Neurons With Brain Derived Neurotrophic Factor (BDNF) or Dibutyryl (db) cAMP Up-Regulates Arginase I RNA Levels In Cerebellar Neurons. RNA isolated from cerebellar neurons without treatment (lane 2), from cerebellar neurons exposed overnight to either BDNF (200 ng/ml) (lane 3) or dbcAMP (1 mM) (lane 4), was reverse, transcribed and subjected to (A) semi-quantitative PCR; or (B) quantitative PM; using primers specific for arginase I. As a positive control, RNA isolated from liver tissue was subjected to RT PCR and quantitative PCR procedures using the same primers ((A), lane 1; (B), "Liver")
Figure 4B:
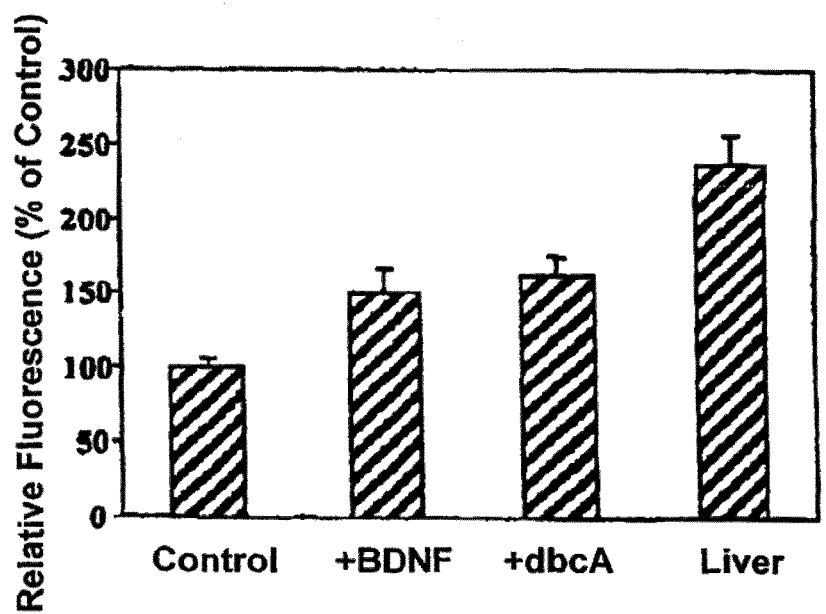

As shown in FIG. 4(*a*), lane 1, there are significant levels of Arg I RNA detected in liver, a positive control. There is also detectable Arg I RNA in cerebellar neurons (lane 2). Levels of Arg I RNA increased after exposure of the neurons to either BDNF (lane 3) or dbcAMP (lane 4). FIG. 4(*b*) shows by quantitative PCR that there was about 2-fold less Arg I RNA in untreated cerebellar neurons as in liver. After treatment of cerebellar neurons with either dbcAMP or BDNF, the amount of Arg I increased significantly (P<0.005) by about 50%.

These results demonstrate that treatment of cerebellar neurons with either dbcAMP or a neurotrophin (BDNF) induces an up-regulation of RNA encoding arginase.

We next assessed the expression of ArgI in cerebellar neurons at the protein level. After exposure of cerebellar neurons to either dbcAMP or BDNF for various times, neurons were lysed, proteins were extracted and the extracted proteins were separated by SDS PAGE before being transferred to membrane and immunostained with a polyclonal antibody against arginase I (see Example 2).

Figure 5A:
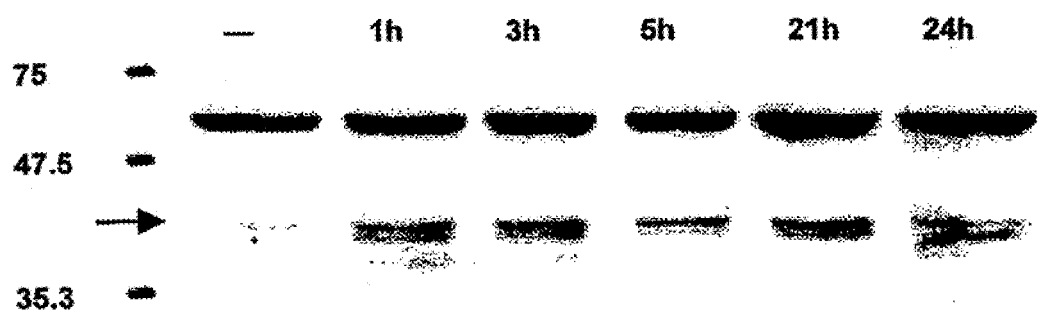
FIG. 5: Arginase I Protein Is Up-Regulated In Cerebellar Neurons After Treating with dbcAMP, BDNF or GDNF For Various Times. Cerebellar neurons were untreated (−) or exposed to either (A) 200 ng/ml BDNF or (B) 1 mM dbcAMP for 1 hour (h), 3 h, 21 h or 24 h; or (C) 200 ng/ml GDNF (+) for 1 h, 3 h or 5 h and the cells lysed in the presence of protease inhibitors. Total protein (23 µg) was subjected to SDS-polyacrylamide gel (12%) electrophoresis (SDS-PAGE), transferred to nitrocellulose membrane and immunostained with antibody to Arg I. The arrows indicate the position of ArgI polypeptide.
Figure 5B:
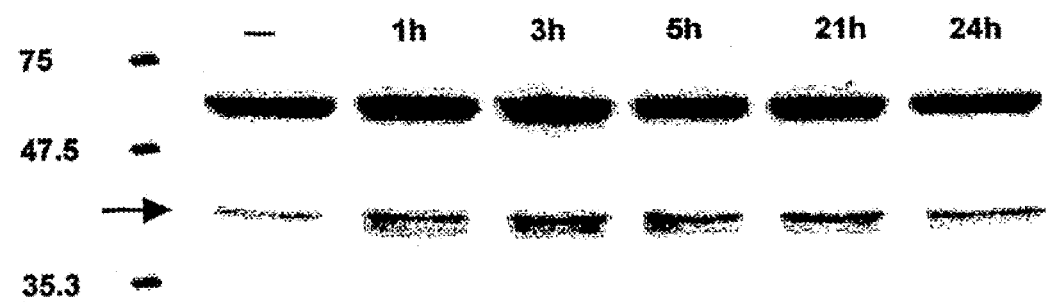
Figure 5C:
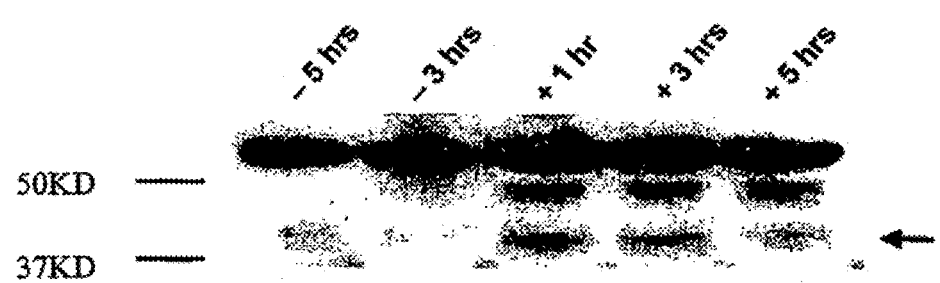

As shown in FIG. 5, arginase I (ArgI) protein is barely detectable in cerebellar neurons (arrows). After 1 hour of exposure of cerebellar neurons to either dbcAMP (A) or BDNF (B), the amount of ArgI proteins increased at least two-fold. This increase peaked around 3 hours post-treatment, and was sustained for 21 hours. By 24 hours after either treatment, the levels of ArgI proteins began to decline. Interestingly, there was a doublet of protein bands detected in cerebellar neurons at the predicted molecular weight; 36 Kda, for ArgI whereas usually only one protein band was detected in liver using the same polyclonal antibody against ArgI (Esch et al., *J. Neuroscience,* 18, pp. 4083-4095 (1998)). We have observed that arginase I in neurons customarily migrates as a doublet when analyzed by SDS PAGE. The doublet likely reflects a post-translational modification of the native arginase I (e.g., a deletion of one or more amino acids and/or addition of chemical modifications such as glycosylation, phosphorylation, methylation, and the like). It is possible that there is more than one isoform of ArgI in the nervous system, one of which may be a brain-specific. It is noteworthy that there is another protein detected by this anti-ArgI polyclonal antibody which migrates at about 60 Kda whose expression level in cerebellar neurons did not differ with or without BDNF or dbcAMP treatment. This protein thus serves as a reliable internal control for the amount of protein loaded in each lane of the gel.

Neurotrophins have been, classified into different families. Brain-derived neurotrophic factor (BDNF) belongs to the Trk-family of neurotrophins, which includes nerve growth factor (NGF), neurotrophin-3 (NT-3) and neurotrophin 4/5 (NT4/5). The Trk-family neurotrophins act through their signaling Trk tyrosine kinase receptors (TrkA, TrkB, and TrkC) and, in addition, they share a common low affinity receptor, p75. Besides their well-established actions in regulating cell survival, differentiation and proliferation, these Trk-family neurotrophins are involved in processes of neuronal plasticity ((Jelsma and Aguayo, *Curr. Opin. Neurobiol.,* 4, pp. 717-725 (1994); Thoenen, *Science,* 270, pp. 593-598 (1995); each of which is incorporated herein by reference). To ask whether arginase expression is up-regulated upon exposure of neurons to neurotrophins belonging to different molecular families, we next treated cerebellar neurons with glial cell line-derived neurotrophic factor (GDNF).

GDNF was initially identified as a specific trophic factor capable of supporting embryonic ventral midbrain neuronal survival (Lindsay, *Nature,* 373, pp. 289-290 (1995); incorporated herein by reference). Subsequently, it has been shown that GDNF has protective effects on axotomized motor neurons from facial nucleus and spinal cord, as well as on sympathetic, sensory and ciliary neurons from the peripheral nervous system (PNS) (Mason, *Mol. Cell Neurosci.,* 8, pp. 112-119 (1996); incorporated herein by reference). Further studies have expanded the GDNF-like family to four members: in addition to GDNF, neurturin (NRTN), arternin (ARTN) and persephin (PSP) are also identified. This family of neurotrophins acts through a multicomponent receptor system, distinct from Trk receptors, comprising a high-affinity ligand-binding co-receptor GFR (GDNF family receptor component) and the Ret tyrosine kinase (Baloh et al., *Curr. Opin. Neurobiol.,* 10, pp. 103-110 (2000); incorporated herein by reference).

Cerebellar neurons were untreated (−) or exposed to 200 ng/ml GDNF for 1 h, 3 h or 5 h and the cells lysed in the presence of protease inhibitors. Total protein (23 μg) was subjected to SDS-polyacrylamide gel (12%) electrophoresis (SDS-PAGE), transferred to nitrocellulose membrane and immunostained with antibody to Arg I. As shown in FIG.

5(C), the amount of ArgI polypeptide increased at least two-fold after treatment of neurons with GDNF.

Together, the results shown in FIG. 4 and FIG. 5 show that exposure of cerebellar neurons to either dbcAMP or members of two distinct neurotrophin families (BDNF and GDNF)—each of which increases endogenous cAMP levels—results in up-regulation of the enzyme arginase I at both the RNA and protein levels. This is the first time that cAMP has been shown to induce expression of arginase in neurons.

Figure 6A:
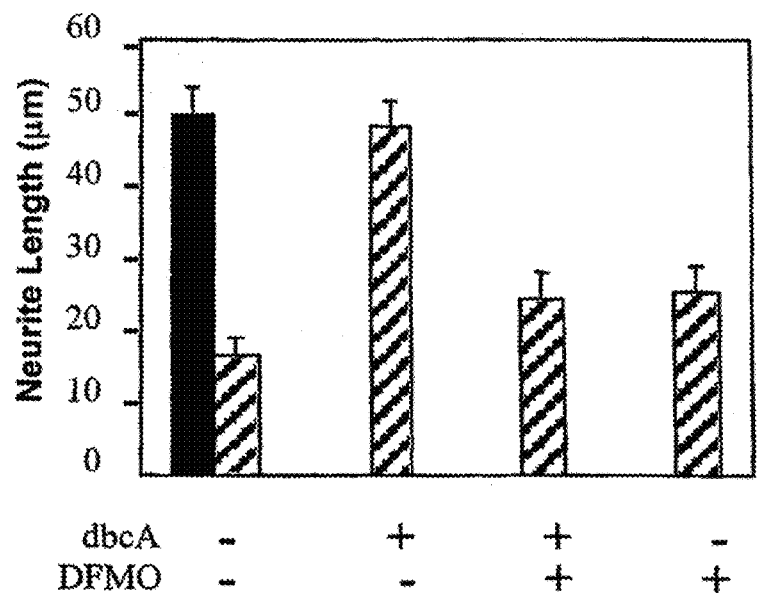
FIG. 6: An Ornithine Decarboxylase (ODC) Inhibitor Abrogates the Blocking Effect of dbcAMP on the Inhibition of Axonal Outgrowth by MAG and Myelin. Cerebellar neurons were plated onto (A) MAG-expressing CHO (striped bars) or control CHO (black bars) cells; or (B) a substrate of purified CNS myelin, in the presence (+) or absence (−) of 1 mM dbcAMP (dbcA) and/or 1 mM DL-a-difluoromethylornithinehydrochloride (DFMO), and cultured overnight before being fixed and immunostained for GAP43. The longest neurite from at least 180-200 neurons were measured. Results are shown as the mean neurite length+/−SEM.
Figure 6B:
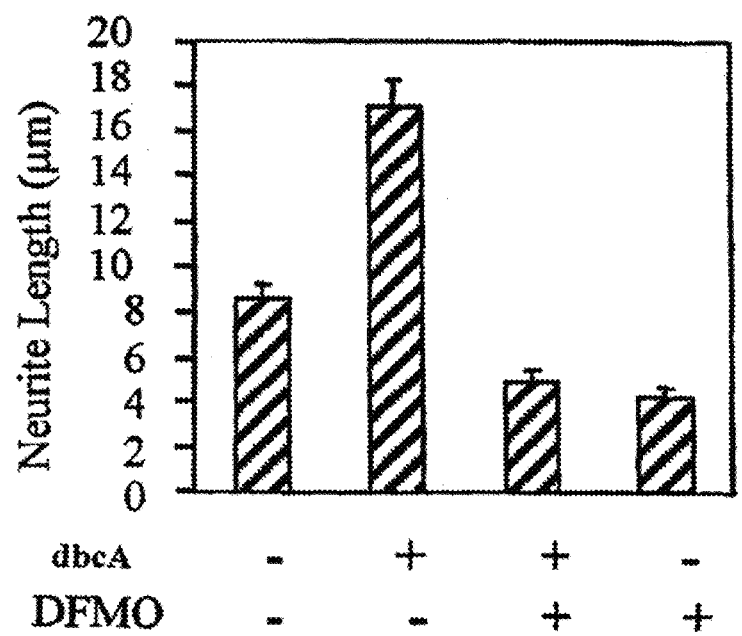

To determine whether the up-regulation of ArgI induced by BDNF, GDNF or dbcAMP is important in the cAMP-mediated block of inhibition of axonal growth by MAG or myelin, we added to the assay an inhibitor of the enzyme ornithine decarboxylase (ODC), which acts one step downstream from arginase in the polyamine biosynthetic pathway (see FIG. 1). A specific ornithine decarboxylase inhibitor, DL-a-difluoromethyl-ornithine hydrochloride (DFMO), was included with BDNF or dbcAMP in neuron growth assays as described above (Examples 1 and 2): As shown in FIG. 6 and discussed above, addition of dbcAMP blocks the inhibition of neurite growth by MAG (A) or myelin (B) (compare (−) and (+) dbcA in (−) DFMO columns). The block of inhibition caused by addition of dbcAMP is lost when the ODC inhibitor DFMO is included. In the presence of DFMO, (A) MAG and (B) myelin each still inhibit axonal outgrowth whether or not dbcAMP is added (compare (−) and (+) dbcA in (+) DFMO columns). DFMO alone has no significant effect on inhibition by (A) MAG or (B) myelin, nor on neurite growth on control CHO cells (A).

Figure 7A:
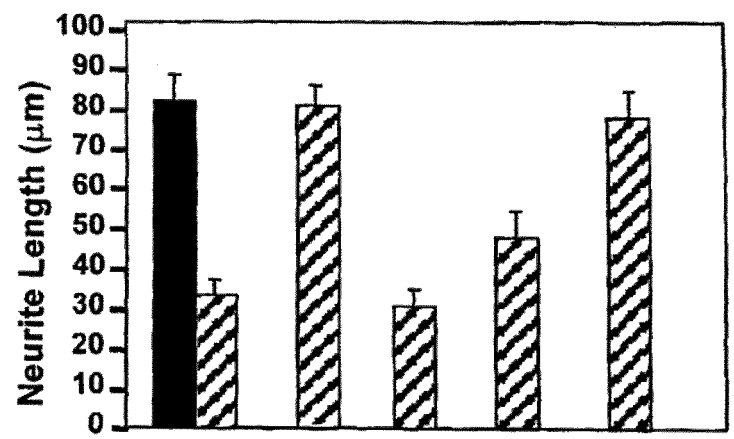
FIG. 7: An Inhibitor of ODC Blocks the Priming Effects of BDNF on the Inhibition by MAG Or Myelin and Putrescine Restores It. Cerebellar neurons were primed overnight with or without BDNF (200 ng/ml), in the presence or absence of DFMO (1 mM), with or without putrescine (10 µM), before being transferred to (A) MAG-expressing (striped bars) or control (black bars) CHO cells; or (B) a substrate of purified CNS myelin. After further incubation, neurons were fixed and immunostained for GAP43. The longest neurite from each neuron for 180-200 neurons were measured. Results are shown as the mean neurite length+/−SEM.
Figure 7B:
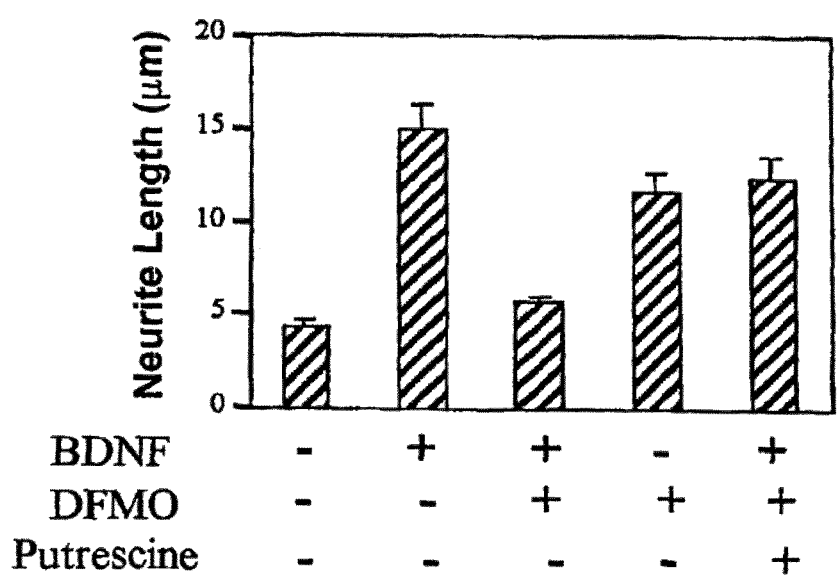

As shown in FIG. 7, when the ODC inhibitor DFMO was included in cultures of cerebellar neurons primed overnight with BDNF, the positive effect of BDNF on axonal growth in the presence of (A) MAG or (B) myelin was completely abrogated and neurite outgrowth remained suppressed. Thus, blocking the conversion of ornithine to putrescine (see FIG. 1) blocks the neurotrophin priming effect on neurite outgrowth. Cerebellar neurons were primed overnight with BDNF, in the presence or absence of DFMO (1 mM), with and without putrescine (10 mM), before being transferred to either (A) MAG-expressing or control CHO cells or (B) CNS myelin. Neurite length was measured as described (Example 1). As before, priming with BDNF blocked the inhibition by MAG. The presence of DFMO during priming abrogated this priming effect and the addition of putrescine, along with DMFO, restored the priming effect of BDNF.

Figure 8:
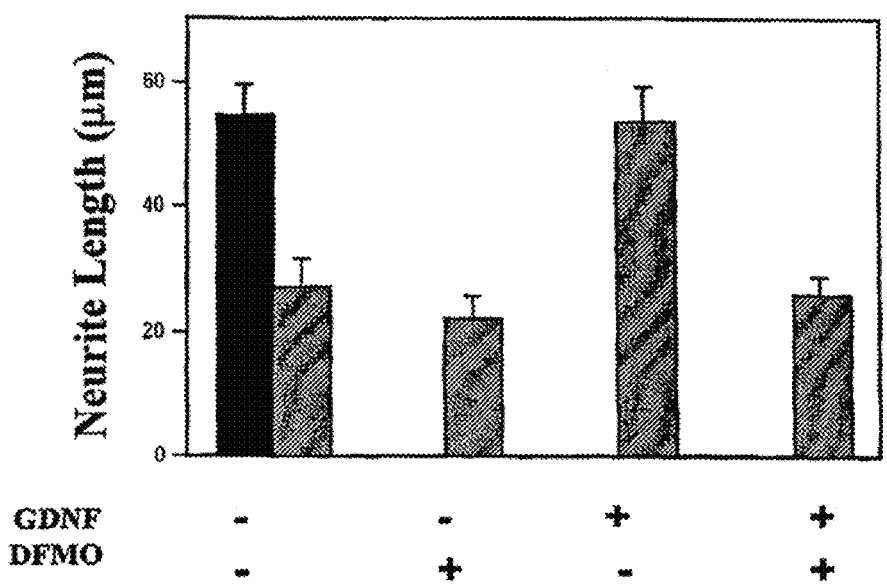
FIG. 8: An Inhibitor Of ODC Blocks The Priming Effects Of GDNF On The Inhibition By MAG. Cerebellar neurons were primed overnight with (+) or without (−) GDNF (200 ng/ml) in the presence (+) or absence (−) of DFMO (1 mM) before being transferred to MAG-expressing (striped bars) or control (black bars) CHO cells. After further incubation, neurons were fixed and immunostained for GAP43. The longest neurite from each neuron for 180-200 neurons were measured. Results are shown as the mean neurite length±SEM.

To test whether the ODC inhibitor DFMO can block the positive effect of GDNF on axonal growth in the presence of MAG, cerebellar neurons were primed overnight with or without GDNF (200 ng/ml), in the presence or absence of DFMO (1 mM) (FIG. 8). Neurite length was measured as described (Example 1). The positive effect of GDNF on axonal growth in the presence of MAG was completely abrogated by blocking ODC and neurite outgrowth remained suppressed. Thus, as was the case for BDNF, blocking the conversion of ornithine to putrescine also blocks the priming effect of GDNF on neurite outgrowth.

We have shown that two neurotrophins, BDNF and GDNF, from two distinct families of neurotrophins, each up-regulate expression of Arg I in neurons and each overcomes inhibition of regeneration by MAG and myelin by priming; an effect that is blocked with the ODC inhibitor DFMO. This implies that two separate families of neurotrophins exert their effects on axonal regeneration on MAG and myelin by acting through Arg I. This has never been shown before and implies that others members of each of these families work in a similar manner.

Figure 9A:
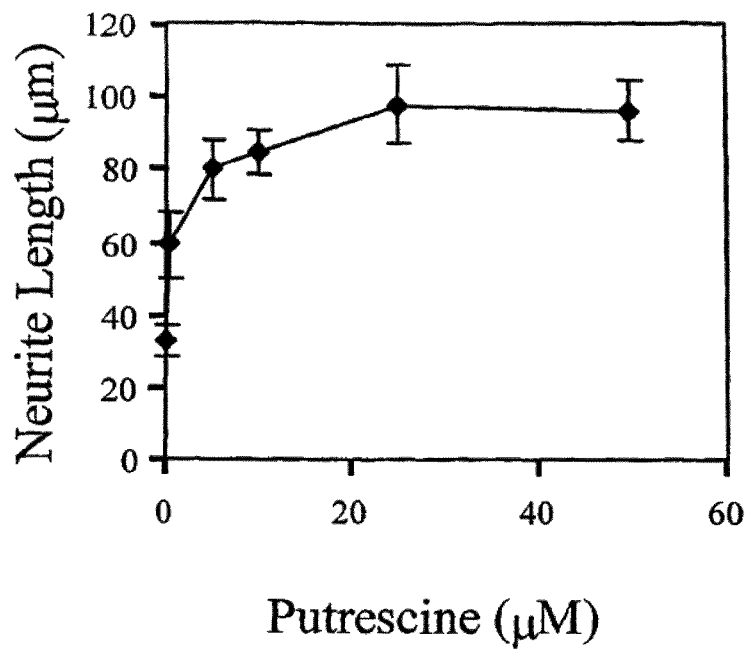
FIG. 9: Putrescine Treatment Alone Is Sufficient To Overcome Inhibition And Allow Subsequent Growth on MAG or Myelin. Cerebellar neurons were primed overnight with putrescine at increasing concentrations ranging from 0-100 µM. Primed neurons were transferred to either MAG-expressing or control CHO cells (A) or a substrate of CNS myelin (B) for further incubation. Neurons were then fixed and immunostained for GAP43. The longest neurite from each neuron was measured for 180-200 neurons. Results are shown as the percentage of control. (A) 100% is the average neurite length+/−SEM of neurons primed without putrescine and subsequently grown on control CHO cells. (B) 100% is the average neurite length+/−SEM of neurons primed without putrescine and subsequently grown on CNS myelin substrate.
Figure 9B:
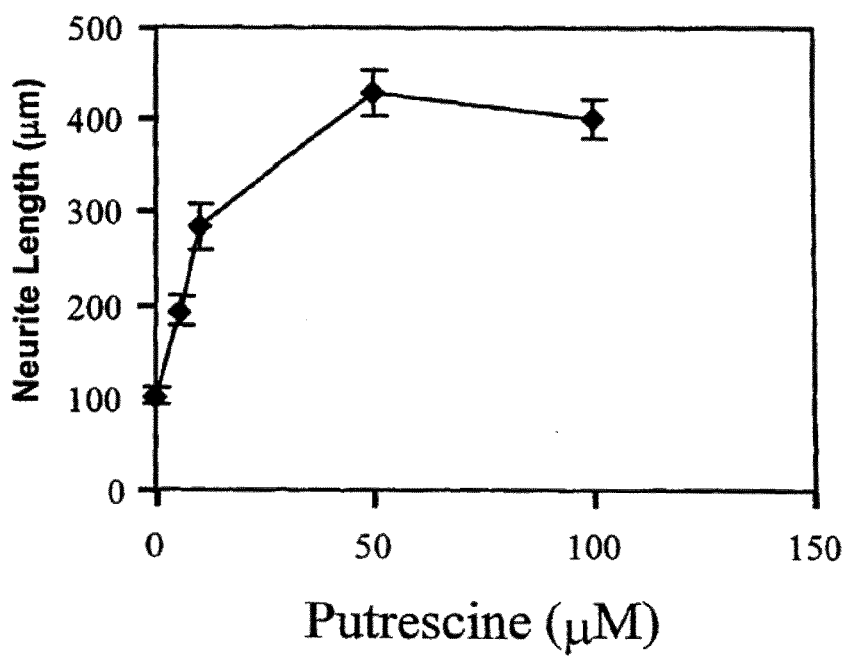

To determine whether putrescine alone can substitute for the neurotrophin priming effect on inhibition by MAG or myelin, neurons were primed with putrescine at different concentrations (FIG. 9). Priming neurons with putrescine in a concentration range of between 10 µM and 25 µM is sufficient to block the inhibitory effect of (A) MAG and (B) myelin on axonal outgrowth. The blocking effect of putrescine on MAG saturates at doses higher than 25 µM. On CNS myelin, priming neurons with putrescine at 10 µM results in at least a two-fold increase in axonal outgrowth, which is similar to the growth from neurons primed with 200 ng/ml BDNF. Priming with putrescine at concentrations between about 10 µM and 50 µM increase axonal growth on myelin even more dramatically. The blocking effect on myelin by priming with putrescine saturates at about 50 µM putrescine. The results are presented as the percentage of control, where 100% is the average neurite length of neurons primed with Sato media only and subsequently grown on (A) control CHO cells or (B) CNS myelin substrate.

To determine whether it is necessary to prime neurons with putrescine in order to completely block axonal growth inhibition by MAG and myelin, cerebellar neurons were grown on MAG-expressing CHO cells or a CNS myelin substrate with different concentrations of putrescine. We found that the addition of putrescine without priming only partially blocks the inhibition of axonal growth by MAG or myelin. In the concentration range of between 15 µM and 100 µM, the blocking effect of putrescine on the inhibition by MAG or myelin reaches a plateau at about 64% reversal.

In summary, the above data suggest that elevation of cAMP, which mediates axonal regeneration in the presence of inhibitory effects of MAG or myelin, induces the up-regulation of arginase at both the transcriptional and translational levels. Arginase performs a limiting step in polyamine synthesis, and perturbations in the polyamine biosynthetic pathway downstream from arginase modulate the ability of axons to grow on MAG or myelin. If the ODC enzyme which acts downstream from arginase is blocked by DFMO, improved axonal growth on MAG or myelin induced by elevated cAMP levels (dbcAMP treatment or neurotrophin (BDNF) priming) is completely abrogated unless exogenous (10 µM) putrescine is added to overcome the ODC block. Importantly, priming with putrescine alone is sufficient to block the inhibition by MAG or myelin in a dose-dependent manner. Thus, manipulations which modulate the levels of putrescine and putrescine-derived polyamines in a neuron will be useful for relieving the inhibition of neurite outgrowth by myelin inhibitors such as MAG.

Sciatic Nerve Transection and Up-Regulation of Arginase

Axons of the CNS usually do not regenerate when cut in vivo. However, for neurons that have two branches, a peripheral and a central branch, such as dorsal root ganglion (DRG) neurons, if the peripheral branch is cut 1 day or 1 week before the central axons are cut, there is considerable regeneration of these CNS axons (Neumann, S. and Woolf; C. J., *Neuron,* 23, pp. 83-91 (1999); Richardson, P. M. and Issa, V. M. K., *Nature,* 309, 791-793 (1984); and Richardson, P. M., et al., *Nature,* 284, pp. 264-265 (1980); each of which is incorporated herein by reference). If the CNS axons of the DRG neuron are cut without a prior conditioning lesion to the peripheral branch, there is no regeneration.

Figure 10:
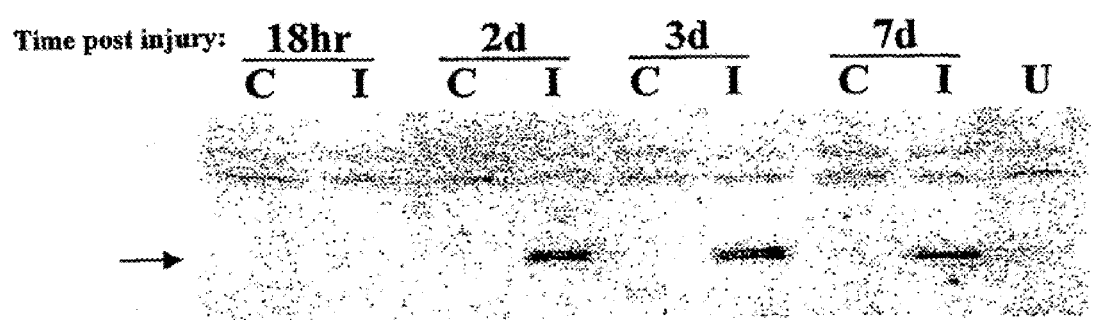
FIG. 10: Arginase Expression Increases After A Conditioning Lesion To The Sciatic Nerve Of DRG Neurons And This Increase Correlates With An Ability To Grow On MAG And Myelin. Left-side sciatic nerve was transected at the mid-thigh level in stage P18 rats. At the times indicated after the injury, dorsal root ganglia (DRG) from the injured side (I) and the uninjured contralateral side (C) were isolated, protein extracted and analyzed by SDS-PAGE and immunoblotting using an anti-arginase I polyclonal antibody. U=unoperated control. The arrow indicates the position of ArgI polypeptide.

We thus wanted to determine whether arginase expression increases after a conditioning lesion to the sciatic nerve of DRG neurons and whether this increase correlates with an ability to grow on MAG and myelin. Left-side sciatic nerve was transected at the mid-thigh level in stage P18 rats (Example 3). At increasing times after the injury (0.5 hr, 1 hr, 4 hr, 8 hr, 18 hr, 2d, 3d and 7d) dorsal root ganglia (DRG) from the injured side (I) and the uninjured contra-lateral side (C) were isolated and analyzed. As shown in FIG. 10, after a conditioning lesion to the peripheral branch of the DRG neuron, the sciatic nerve, the level of cAMP more than doubles and the expression of Arg I increases. The up-regulation of Arg I is likely to account for the regeneration of the CNS axons following a conditioning peripheral branch lesion.

Up-Regulation of Arginase Blocks the Inhibition of Neurite Outgrowth by MAG

To determine whether the up-regulation of arginase is sufficient to overcome inhibition of axonal growth by MAG, we introduced an arginase I cDNA into neurons. To achieve nearly 100% transfection efficiency in post-mitotic cells, several groups have used viral vectors to deliver heterologous proteins into neurons and glia with high efficiency and low toxicity (see, e.g., Ghadge et al., *J. Neurosci.*, 17, pp. 1397-1405 and pp. 8756-66 (1997) incorporated herein by reference). To overexpress arginase in a neuron, we used adenoviral-mediated gene transfer techniques. Adenovirus (Adv) systems have been used extensively to express human as well as non-human proteins. They can be used to infect a broad range of mammalian cells and therefore permit the expression of recombinant proteins in most mammalian cell lines and tissues. They have advantages over retroviruses in that they can infect post-mitotic cells whereas retroviruses cannot.

Figure 11A:
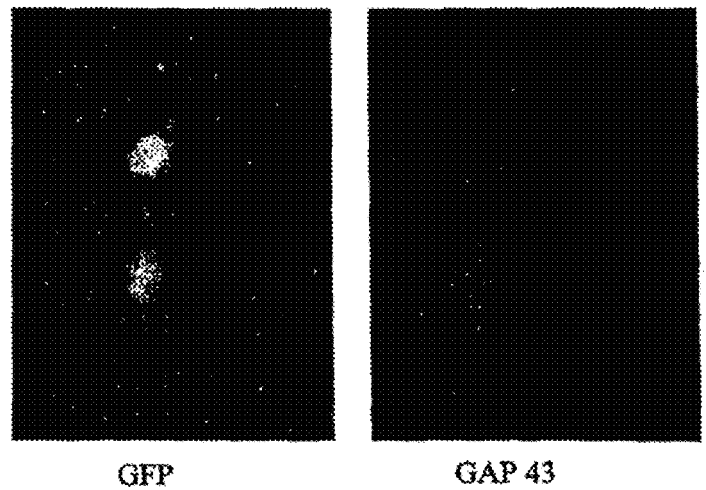
FIG. 11: Over-Expression Of Arginase In Cerebellar Neurons By Adenovirus-Mediated Gene Transfer Is Sufficient To Overcome Inhibition By MAG And Myelin. Cerebellar neurons ($1 \times 10^6$) were plated in 24-well plates and infected with adenovirus containing ArgI-GFP or GFP alone. After overnight culture, infected neurons were transferred to MAG-expressing (stippled bars) or control (black bars) CHO cells for neurite outgrowth. Neurons were fixed and immunostained for GAP43. The neurons with double staining of GAP43 and GFP were considered as positively infected. The length of the longest neurite per neuron was measured for 120-150 positively infected neurons. (A) ArgI-positive infected neurons are double-stained with GAP43 and GFP. (B) The Western Blot of 5 µg of protein lysates from neurons infected with ArgI-adenovirus and GFP only. The arrow indicates the position of ArgI polypeptide. (C) Results are shown as the average neurite length+/−SEM of GFP-infected (GFP) or ArgI-infected (ArgI) neurons grown on MAG.
Figure 11B:
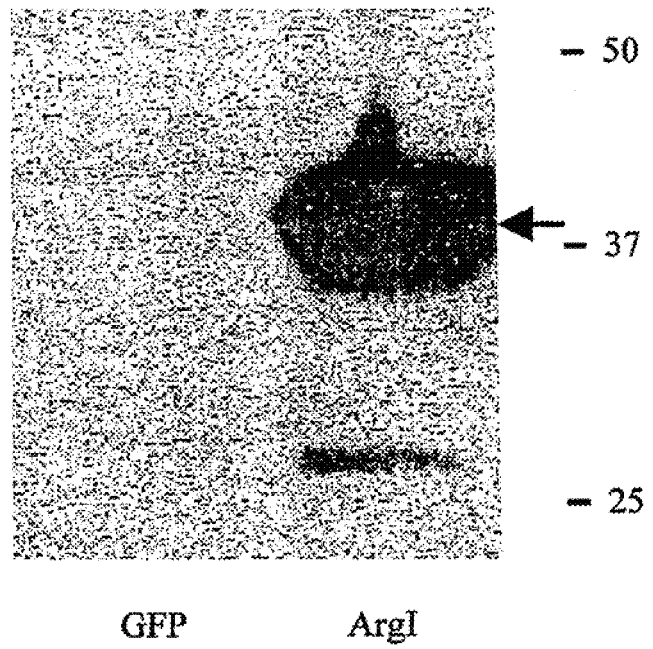

We infected cerebellar neurons with an adenoviral vector encoding the ArgI cDNA and a green fluorescent protein (GFP) marker cDNA (Example 4). As a control, we infected cerebellar neurons with a corresponding adenoviral vector encoding the GFP marker cDNA alone. FIG. 11A shows a neuron that is positively immunostained for GFP and GAP43. FIG. 11B shows cerebellar neuron proteins separated by SDS-PAGE and immunoblotted with ArgI antibodies (Western blot analysis) (Example 4). After infection, there is abundant expression of ArgI (see arrow) in cells infected with the ArgI-GFP adenoviral vector but not with the control GFP vector. The endogenous levels of ArgI are undetectable in 5 µg protein from GFP-adenovirus infected neurons. Arg I was first detected upon loading 23 µg total protein from these control cells.

Figure 11C:
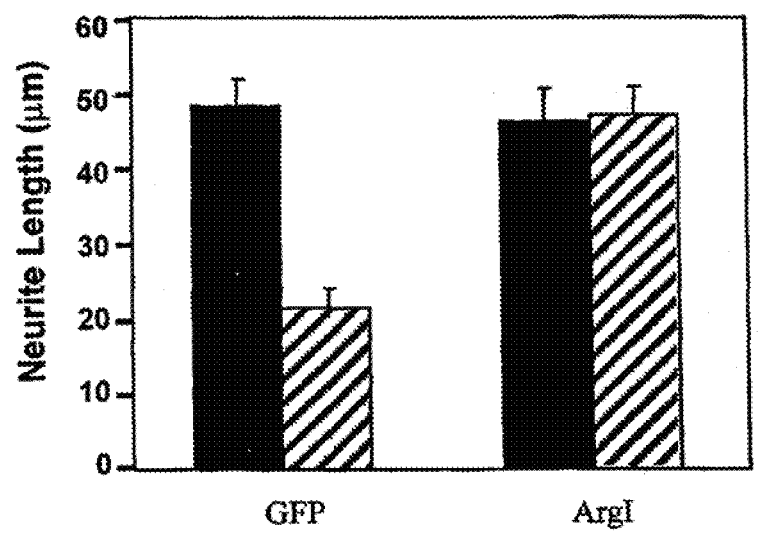

We then compared the axonal growth ability of ArgI/GFP- and GFP-adenovirus infected neurons on MAG-expressing or control CHO cells. As shown in FIG. 11C, axonal outgrowth from cerebellar neurons expressing arginase I (ArgI) is not inhibited by MAG. Control infected neurons expressing GFP alone (GFP) remain subject to MAG-dependent inhibition of axonal growth.

Figure 12:
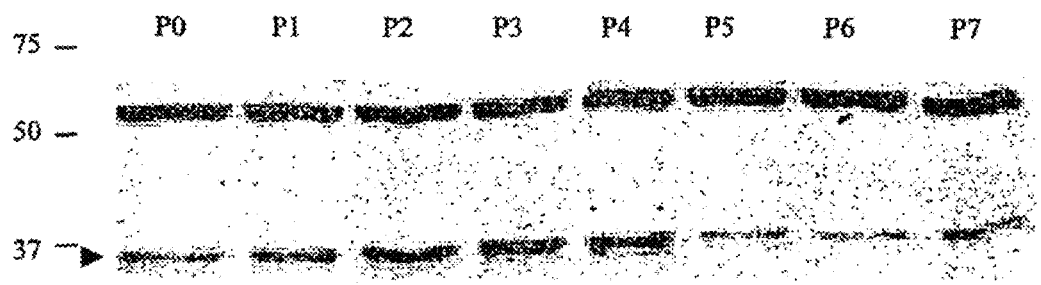
FIG. 12: Expression of Arginase Is High In Young DRG Neurons That Are Not Inhibited By, And Is Lower In Older Neurons That Are Inhibited By, MAG And Myelin. Dorsal root ganglial (DRG) neurons from postnatal day P0-P7 were isolated and lysed with RIPA buffer. The 32 µg of total proteins were subjected to SDS-PAGE (12%) before being transferred to nitrocellulose membrane and immunostained with antibody against ArgI. The arrow indicates the position of ArgI polypeptide.

In summary, elevation of cAMP induces up-regulation of arginase I and over-expression of arginase I is sufficient to overcome the inhibition of axonal growth by MAG. Because endogenous cAMP levels correlate with neuronal regenerative capacity during development and after injury, we asked whether endogenous expression levels of ArgI in neurons correlates with neuronal regenerative capacity. Dorsal root ganglia (DRG) neurons from different postnatal days (between P0 and P7) were isolated and total proteins were extracted. Endogenous Are protein levels at different postnatal ages was examined by Western blot analysis. (Example 4). As shown in FIG. 12, ArgI protein levels in DRG neurons at stages P0-P4 are more abundant than in postnatal cerebellar neurons (FIG. 5). Sometime between postnatal days 4-5 in DRG neurons, however, there is a sharp decrease in ArgI protein levels and this low level persists to late postnatal ages. The drop in endogenous ArgI proteins in DRO neurons is similar to the previously noted decrease of endogenous cAMP during development which correlates with a loss of regenerative capacity in the presence of MAG or myelin. It was thus possible that modulating ArgI levels in developing DRG neurons could affect their regenerative capacity.

Figure 13:
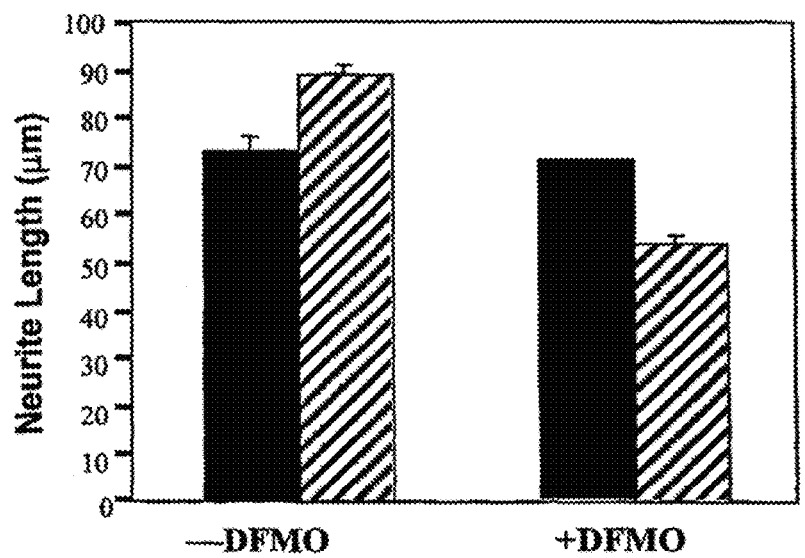
FIG. 13: The Ability Of Young DRG Neurons To Grow On MAG And Myelin Is Blocked By The ODC Inhibitor, DFMO. Postnatal day 1 (P1) DRG neurons were isolated and plated on MAG-expressing (stippled bars) or control (black bars) CHO cells, with (+) or without (−) 1 mM DFMO. After overnight incubation, neurons were fixed and immunostained for GAP 43. The longest neurite from each of 120-150 DRG neurons were measured. Results are shown as the mean neurite length+/−SEM.

DRG neurons have been shown to switch their axonal regenerative response to MAG and myelin from promotion to inhibition during development. The transition occurs sharply between postnatal days 3-4 (DeBellard et al., *Mol. Cell. Neurosci.*, 7, pp. 89-101 (1996)). To determine whether promotion of axonal growth from P0-P1 DRG neurons by MAG can be blocked if a step in the polyamine biosynthetic pathway downstream from arginase is blocked, P0/1 DRG neurons were isolated and cultured on MAG-expressing CHO cells in the presence of the irreversible ODC inhibitor DFMO (see supra). As shown in FIG. 13, promotion of P0-1 DRG neurons by MAG is completely abolished (and even slightly reversed) by adding the ODC inhibitor DFMO-axonal growth in the P0-1 DRG neurons is slightly inhibited rather than promoted by MAG. The DFMO effect is MAG-dependent because DFMO alone has no effect on neurite growth on control CHO cells. Thus in young DRG neurons, blocking a step downstream from arginase in the polyamine biosynthetic pathway can switch the neuronal response to MAG from promotion to inhibition.

Figure 14:
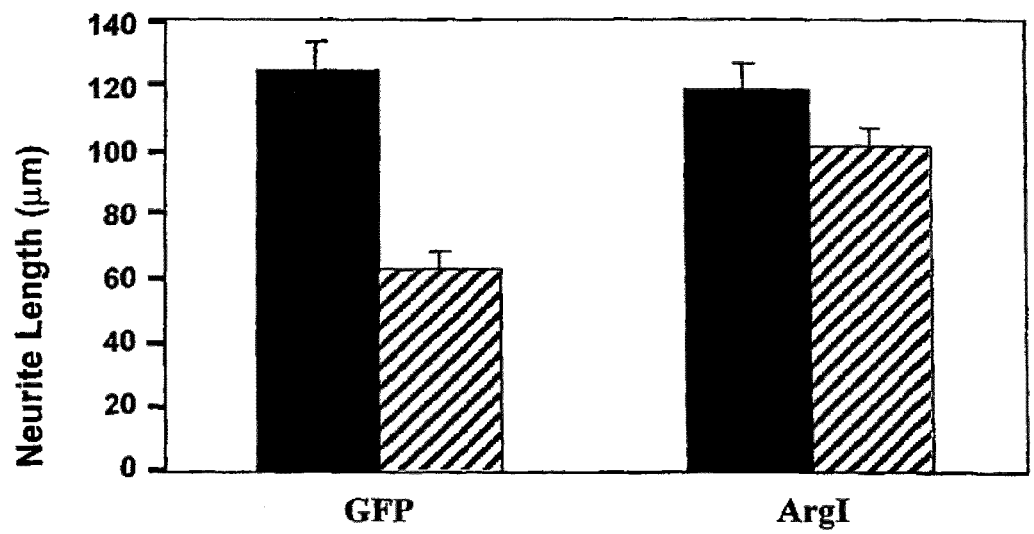
FIG. 14: Over-Expression Of Arginase In Older DRG Neurons By Adenovirus-Mediated Gene Transfer Is Sufficient To Overcome Inhibition By MAG. Postnatal day 5 DRG neurons ($0.5 \times 10^6$) were plated in 24-well plates and infected with adenovirus containing ArgI-GFP or GFP alone. Alter overnight culture, infected neurons were transferred to MAG-expressing (stippled bars) or control (black bars) CHO cells for neurite outgrowth. Neurons were fixed and immunostained for GAP43. The neurons with double staining of GAP43 and GFP were considered as positively infected. The length of the longest neurite per neuron was measured for 120-150 positively infected neurons. Results are shown as the average neurite length+/−SEM of GFP-infected (GFP) or ArgI-infected (ArgI) neurons grown on MAG.

To determine if increasing the expression levels of Arg I in older DRG neurons is sufficient to block the inhibitory effect of MAG on axonal growth, we used adenoviral-mediated ArgI gene transfer to introduce ArgI cDNA sequences into DRG neurons at post natal day 7 (PND7) (Example 4). FIG. 14 shows that over-expression of ArgI in DRG neurons relieves MAG-dependent inhibition of axonal growth. Neuronal outgrowth capacity on MAG is significantly improved by increasing ArgI levels.

These results show that expression levels of ArgI in neurons correlate with the developmentally regulated capacity of neurons to grow axons in response to MAG. In young neurons, endogenous cAMP and ArgI levels are high and axonal growth from these neurons is promoted by MAG. During neuronal development, there is a decrease in the ArgI expression levels which coincides with decreases in endogenous cAMP levels. Subsequent to this developmental switch, axonal growth from neurons is inhibited rather than promoted by MAG. Therefore, by changing the cAMP or ArgI expression levels in neurons, the developmental switch of neuronal responses to MAG may be modulated. The level and direction of desired modulation of polyamine levels or of arginase activity will thus depend on the cell type and the developmental stage of the targeted neuron.

Importantly, arginase also plays an important role in anti-apoptotic and other neuronal cell death mechanisms and is likely to be involved in neurodegenerative diseases such as amyotrophic lateral sclerosis, Alzheimer's disease, Parkinson's disease, Huntington's disease, multiple sclerosis, and the like (infra). It follows that modulation of neuronal polyamine levels by altering putrescine or arginase activity will be therapeutic in these diseases as well as in the treatment of spinal cord injury and other nervous tissue damage.

Together, the results show for the first time that elevating cAMP in neurons, either artificially with db cAMP or by priming with neurotrophin, induces the up-regulation of the enzyme arginase, which in turn activates the pathway for the synthesize of putrescine and other polyamines. These polyamines are responsible, at least in part, for the cAMP-induced block of inhibition by myelin and MAG (FIG. 9). Arginase activity and putrescine levels are, therefore, likely to be a key factor in changing the intrinsic growth capacity of adult neurons such that they are no longer inhibited by MAG and myelin and so regenerate after injury in vivo. It is known that if inhibitors of regeneration present in myelin are blocked immediately after injury, regeneration can occur. Therefore, artificially up-regulating arginase activity in a neuron after injury in vivo is likely to allow regeneration to occur. Alternatively, down-regulating arginase activity is likely to block regeneration in vivo, which may be desirable under certain circumstances. Treatment of neurons with putrescine, or putrescine analogs or derivatives, are also expected to have such effects.

Agents that Affect Putrescine and Polyamine Levels in Neurons

As shown above, addition of putrescine to adult neurons can relieve inhibition by myelin (and MAG) of neuronal growth. Putrescine, and putrescine analogs and derivatives which, for example, have longer half-lives, greater bioavailability, and the like, will therefore be useful in compositions and therapeutic methods according to the present invention. The invention thus provides compositions and methods for increasing endogenous putrescine (and derivative polyamine) levels in the cells of the nervous system.

Putrescine may be administered directly to the cerebrospinal fluid (CSF) by, for example, by epidural or intrathecal pump or lumbar puncture. For intrathecal or epidural administration, see, e.g., Bragg, C. Practical aspects of epidural and intrathecal narcotic analgesia in the intensive care setting. *Heart Lung,* 18(6), pp. 599-608 (1989); and Coombs, D. W. et al., Relief of continuous pain by intraspinal narcotics via an implanted reservoir. *JAMA,* 250, pp. 2336-2339 (1984); each of which is incorporated herein by reference. Alternatively, neural or glial cells of the nervous system may be engineered to express altered (e.g., higher) levels of putrescine and other derivative polyamines. For example, the enzyme ornithine amino transferase (OAT) converts ornithine into pyrroline-5-carboxylate. Inhibitors of OAT, such as 5-fluoro-methylornithine, would be expected to increase the levels of ornithine available for polyamine synthesis. (*J. Mol. Biol.,* 285, pp. 297-309 (1999)). Such OAT inhibitors would thus constitute a putrescine or derivative polyamine modulatory agent useful for practicing the present invention.

As described below, another method modulating putrescine and derivative polyamine levels in a neuron is by modulating arginase activity in the cell according to the methods of the invention (see below). Such methods comprise the step of administering a composition according to the invention comprising an arginase modulatory agent. Such methods optionally further comprise the step of monitoring the growth of at least one neuron following administration of a compound of the invention.

Arginase Modulatory Agents

Arginase Nucleic Acids and Polypeptides—

Human, rat and mouse arginase I and II cDNAs have been isolated and characterized (see below). Arginase polypeptides of the same isoform type (type I or II) are approximately 85%-95% identical to each other at the amino acid level. Mammalian arginase I and II polypeptides are approximately 70% identical at the amino acid sequence level and differ primarily in that arginase II has a mitochondrial protein targeting sequence. (See, e.g., Morris et al., gene, 193, pp. 157-161 (1997); see also NCBI GenBank accession numbers NP 000036.2 and AAH01350.1 for human arginase I and II polypeptide sequences, and NM 00045 and 001172 for human arginase 1 and II cDNA sequences, respectively, which are incorporated herein by reference).

A comparison of arginase sequences from the livers of rat, human, *Xenopus laevis,* yeast and *Agrobacterium* TiC58 plasmid has revealed three conserved histidine residues within a 40-residue segment. In human and rat arginases, the conserved histidine residues are found at amino acid residues 101, 126 and 141 within conserved amino add sequences at positions 98-107, 122-131 and 137-146 (Cavalli et al., Biochemistry, 33, pp. 10652-10657 (1994)). It is thus anticipated that polypeptide muteins, fragments, analogs, fusions, derivatives and the lace, which comprise conserved amino acid residues 98-107, 122-131 and 137-146 of arginase at those or different positions (or conservative substitutions of the non-histidine residues within those conserved regions such that at least 70% amino acid sequence identity remains) will retain arginase activity and will be useful in the compositions and methods of the present invention.

Likewise, it is anticipated that related polypeptides having arginase activity which belong to the above described family of mammalian arginase proteins (i.e., which are at least about 70% identical to each other at the amino acid level, preferably 85%-95% identical to each other at the amino acid level) will be useful in practicing the present invention. The GenBank public database (accessible at www.ncbi.nlm.inh.gov), for example, contains 479 sequence entries that are classified as arginase and arginase-related, 294 of which are found with the search term "arginase mammalia". An arginase family has recently been defined by sequence comparisons and three dimensional sequence alignments between eukaryotic and bacterial arginases, which can be found at (www.nebi.nlm.nih.gov/Structur ekdd/cddsrv.cgi?uid=pfam00491).

The present invention thus provides polynucleotides, including single- and double-stranded DNA and RNA (sense or antisense) which are capable of modulating arginase activity in a neuron. The nucleic acid sequences may be used directly to modulate arginase activity in the nervous system, e.g., by expression of a polypeptide having arginase activity, or by expression of an antisense nucleic acid that inhibits arginase activity, in a neuron or glial cell. Preferably, arginase nucleic acid sequences that encode a polypeptide comprising the conserved amino acid residues 98-107, 122-131 and 137-146 of human or mammalian arginase I are used. Alternatively, nucleic acid sequences that encode a polypeptide comprising one or more conservative substitutions of the non-histidine residues within amino acid residues 98-107, 122-131 and 137-146 of human or mammalian arginase I such that at least 70% amino acid sequence identity remains between residues 98 and 146; or those that can hybridize under stringent conditions to a nucleic acid sequence encoding a polypeptide comprising the conserved amino acid residues 98-107, 122-131 and 137-146 of human or mammalian arginase I are used.

The cDNAs encoding the known mammalian arginase enzymes (rat, mouse and human) are approximately 50% identical at the nucleic acid level. Expression of any one of these arginase nucleic acids in a neuron, or in a cell which can provide subsequent arginase activity to a neuron, is thus expected to be useful for modulating arginase activity according to the present invention. Likewise, it is expected that nucleic acid sequences related by at least 50% sequence identity to those sequences, especially those which comprise sequences that encode the conserved amino acid residues of arginase as discussed above, will be useful in practicing the present invention.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence. Useful expression vectors, for example, may consist of segments of chromosomal, non-chromosomal and synthetic nucleic acid sequences.

A wide variety of host/expression vector combinations may be employed in expressing the polynucleotide sequences which act as arginase modulatory agents of the invention. Such host/expression vector combinations are well-known in the art and may be selected, for example, based on the host cell type chosen as a target for gene delivery. Preferably, the host cell will be a mammalian host cell. In some embodiments, the host cell may be engineered to constitutively express the arginase modulatory agent of the invention. In alternative embodiments, the host cell may be engineered to express the arginase modulatory agent in a regulated fashion, e.g., upon receiving a molecular signal such as the presence or absence of a regulatory molecule required for activation by expression control sequences. The host cell may be one that is grown in culture and then introduced into a subject or patient in need of treatment, Alternatively, the host cell may be one that resides in or is otherwise in communication with a part of the nervous system of the subject or patient in need of treatment.

In preferred embodiments, eukaryotic cells, and more preferably, mammalian cells may be used as host cells. Expression in mammalian cells can be achieved using a variety of plasmids, including pSV2, pBC12BI, and p91023, as well as lytic virus vectors (e.g., vaccinia virus, adenovirus, AAV and baculovirus), episomal virus vectors (e.g., bovine papillomavirus), and retroviral vectors (e.g., murine retroviruses and HIV), including lentivectors (see, e.g., Consiglio et al., Nature Med., 7, pp. 310-316 (2001), incorporated herein by reference). Useful vectors for insect cells include baculoviral vectors and pVL 941. These and other viral and non-viral vectors are well-known to those of skill in the art of nucleic acid delivery and expression in eukaryotic cells.

In addition, any of a wide variety of expression control sequences may be used in these vectors to express the polynucleotide sequences of this invention. Such useful expression control sequences include the expression control sequences associated with structural genes of the foregoing expression vectors. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation.

Expression control sequences may also include sequences that target a nucleic acid or protein to a particular sub-cellular location or compartment, e.g., mitochondrial target sequences, nuclear localization sequences, cytoplasmic retention sequences, and secretion sequences which target a protein to the endoplasmic reticulum and thus the secretion pathway of the host cell. The properties of such sequences and how they can be derived from available materials are well-known and will be appreciated by those of skill in the art.

Examples of useful expression control sequences include, for example, the early and late promoters of SV40 or adenovirus, splicing sequences of SV40, the CMV promoter/enhancer, the T3 and T7 promoters, the promoter for 3-phosphoglycerate kinase or other glycolytic enzymes, the promoters of acid phosphatase, e.g., Pho5, the promoters of the yeast α-mating system, the GAL1 or GAL10 promoters, and other constitutive and inducible promoter sequences known to control the expression of genes of prokaryotic or eukaryotic cells or their viruses, and various combinations thereof appropriately modified to act in the selected host cell. Promoters that may be induced in the brain include but are not limited to those described in Chen et al., Mol. Pharmacol., 54, pp. 495-503 (1998); and Tremblay et al., Proc. Natl. Acad. Sci. 95, pp. 12580-12585 (1998); each of which is incorporated herein by reference. Those of skill in the art will immediately appreciate how to identify and use other expression control sequences that may be used to achieve regulated gene expression in cells of the brain and nervous system.

Preferred nucleic acid vectors also include a selectable or amplifiable marker gene and means for selecting or amplifying the copy number of the gene of interest. Such marker genes are well-known in the art. Nucleic acid vectors may also comprise stabilizing sequences (e.g., ori- or ARS-like sequences and telomere-like sequences), or may alternatively be designed to favor directed or non-directed integration into the host cell genome. In a preferred embodiment, nucleic acid sequences of this invention are inserted in frame into an expression vector that allows high level expression of an RNA which encodes a protein comprising the encoded nucleic acid sequence of interest. Nucleic acid cloning and sequencing methods are well known to those of skill in the art and are described in an assortment of laboratory manuals, including Ausubel et al., (supra). Product information from manufacturers of biological, chemical and immunological reagents also provide useful information.

Of course, not all vectors and expression control sequences will function equally well to express the nucleic acid sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered.

Transformation and other methods of introducing nucleic acids into a host cell (e.g., conjugation, protoplast transformation or fusion, transfection, electroporation, liposome delivery, membrane fusion techniques, high velocity DNA-3.0 coated pellets, viral infection and protoplast fusion) can be accomplished by a variety of methods which are well known in the art (see, for instance, Ausubel, supra). Bacterial, yeast, plant or mammalian cells are transformed or transfected with an expression vector, such as a plasmid, a cosmid, or the like, wherein the expression vector comprises the nucleic acid of interest. Alternatively, the cells may be infected by a viral expression vector comprising the nucleic acid of interest. Depending upon the host cell, vector, and method of transformation used, transient or stable expression of the nucleic acid and an encoded polypeptide, will be constitutive or inducible. One having ordinary skill in the art will be able to decide whether to express a polynucleotide or polypeptide transiently or stably, and whether to express an encoded protein constitutively or in a regulated fashion (e.g., inducibly).

A wide variety of unicellular host cells are useful in expressing the DNA sequences of this invention. These hosts may include well known eukaryotic and prokaryotic hosts, animal cells such as CHO, BHK, MDCK and various murine cells, e.g., 3D and WEHI cells, African green monkey cells such as COS 1, COS 7, BSC 1, BSC 40, and BMT 10, and human cells such as VERO, WI38, and HeLa cells. Useful neural cells include but are not limited to rat hippocampal cell lines such as H19-7, HT-22; human neuroblastoma such as SH-SY5Y; and mouse neuroblastoma cells such as N2a and N18. The invention is in no way envisioned to be limited to the particular host cell selected for expression of an arginase modulatory agent.

Particular details of gene delivery, gene expression and purification of recombinant proteins are well documented and are understood by those of skill in the art. Further details on the various technical aspects of each of the steps used in recombinant production of foreign genes in heterologous cell expression systems can be found in a number of texts and laboratory manuals in the art. See, e.g., Ausubel et al., supra, and Sambrook et al., supra, and Kieser at al., supra, incorporated herein by reference.

Non-Arginase Nucleic Acids and Polypeptides
Arginase Inhibitors and Activators

Ornithine is a known feedback inhibitor of arginase I. It is thus anticipated that molecules which partially or fully inhibit or compete with the ability of ornithine to feedback inhibit arginase I activity will be useful modulators of arginase function in a neuron. Such arginase modulatory molecules may be easily identified by performing classic enzyme substrate inhibition and competition studies using arginase assays in the presence of the arginase inhibitor ornithine and varying concentrations of one or more test compounds. Such arginase modulatory agents may, but need not necessarily, act in a concentration and time dependent manner. Genetic selections and analyses (e.g., looking for mutations that suppress particular phenotypes) in a model genetic organism such as yeast or fruit fly may be used as an alternative to or in conjunction with enzymatic assays to identify arginase modulatory agents.

Finally, a number of arginase inhibitors have been identified. 2(S)-amino-6-boronohexanoic acid, for example, a boronic add-based arginine analog, can inhibit arginase in vivo (Cox et al., *Nature Struct. Biol.*, 6, pp. 1043-1047 (1999), incorporated herein by reference). These researchers have determined the X-ray crystal structure of arginase bound to the inhibitor 2(S)-amino-6-boronohexanoic acid (also known as ABH). These structural results indicate that ABH mimics the first step in the arginase enzymatic reaction and thus help to explain why ABH is the most potent inhibitor of arginase identified to date. N(omega)-hydroxy-1-arginine (LOHA) is another example of an arginase inhibitor (Iniesta et al., *J. Exp. Med.*, 193, pp. 777-784 (2001), incorporated herein by reference). See also Khangulov et al., *Biochemistry*, 37(23), pp. 8539-50 (1998), incorporated herein by reference). Any arginase inhibitor may be used as an arginase modulatory agent, or may be used to identify agents such as small molecules which are capable of relieving arginase inhibition in vivo and which are thereby arginase modulatory agents according to the present invention.

Pharmaceutical Compositions and Treatments Using Neuronal Polyamine and Arginase Modulators The putrescine, derivative polyamine and arginase modulatory agents of this invention may be formulated into pharmaceutical compositions and administered in vivo at effective dose to treat the particular clinical condition addressed. Administration of one or more of the pharmaceutical compositions according to this invention will be useful for regulating, e.g., for promoting or inhibiting neural growth or regeneration in the nervous system, for treating injuries or damage to nervous tissue or neurons, and for treating neural degeneration associated with injuries (such as traumas) to the nervous system, disorders or diseases, including those associated with apoptosis, necrosis or other forms of cell death. Such injuries, diseases or disorders include spinal cord injury, brain injury, aneurysms and strokes. Such injuries, diseases or disorders also include PNS injury, viral infection (e.g., by herpes virus or HIV), encephalitis (viral or non-viral), mitochondrial disease, Creutzfeldt-Jacob disease, kuru, multiple system atrophy, multiple sclerosis, peripheral neuropathies and progressive supranuclear palsy.

Neurodegenerative diseases include, but are not limited to: amyotropic lateral sclerosis (Lou Gebrig's disease; "ALS"); Parkinson's Disease; Parkinson's Plus Syndromes; ALS-Parkinson dementia complex Huntington's Disease; Alzheimer's Disease; Pick Disease; Wilson's Disease; hepatolenticular degeneration; environmental toxins, including manganese and carbon monoxide poisoning; inherited epilepsies; nutritional deficiency states (e.g., Wernicke-Korsakoff syndrome, B12 deficiency and pellagra); prolonged hypoglycemia or hypoxia; paraneoplastic syndromes; heavy metal exposure (e.g., arsenic, bismuth, gold, manganese and mercury); dialysis dementia; Schilder lipid-storage diseases; cerebrocerebellar degeneration; dementia with spastic paraplegia; progressive supranuclear palsy; Binswanger Disease; brain tumor or abcess; Marchiava-Bignami Disease, communicating, normal pressure or obstructive hydrocephalus; progressive multifocal leukoencephalitis; Lewy-Body Disease; some cases of AIDS; progressive aphasia syndromes; and frontal lobe dementia. See Principles of Neurology (Sixth Edition), Adams, R. D., Victor, M., and Ropper, A. H. eds. 1997 (McGraw-Hill, New York); incorporated herein by reference in its entirety.

Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment. See, e.g., Handbook of Pharmaceutical Additives: An International Guide to More than 6000 Products by Trade Name, Chemical, Function, and Manufacturer, Ashgate Publishing Co., eds., M. Ash and L Ash, 1996; The Merck Index: An Encyclopedia of Chemicals, Drugs and Biologicals, ed. S. Budavari, annual; Remington's Pharmaceutical Sciences, Mack Publishing Company, Easton, POLYAMINE; Martindale: The Complete Drug Reference, ed. IC. Parfitt, 1999; and Goodman & Gilman's The Pharmaceutical Basis of Therapeutics, Pergamon Press, New York, N. Y., ed. L. S. Goodman et al.; the contents of which are incorporated herein by reference.

Administration of the neuronal polyamine and arginase modulators of the invention, including isolated and purified forms, their salts or pharmaceutically acceptable derivatives thereof may be accomplished using any of the conventionally accepted modes of administration of agents'which are used to treat injuries or disorders, especially those relating to the central and peripheral nervous system.

Formulations

The pharmaceutical compositions of this invention may be in a variety of forms, which may be selected according to the preferred modes of administration. These include, for example, solid, semi-solid and liquid dosage forms such as tablets, capsules, pills, powders, creams, liquid solutions or suspensions, syrups, suppositories, injectable and infusible solutions, aerosols and the like. The preferred form depends on the intended mode of administration and therapeutic application. Modes of administration may include, but are not limited to, oral, parenteral (including subcutaneous, intravenous, intramuscular, intra-articular, intra-synovial, cisternal, intrathecal, intrahepatic, intralesional and intracranial injection or infusion), topical, rectal, nasal, buccal, vaginal, by inhalation, or by an implanted reservoir, external pump or catheter.

The polyamine and arginase modulatory agents of this invention may, for example, be placed into sterile, isotonic formulation with or without cofactors which stimulate uptake or stability. The formulation is preferably liquid, or may be lyophilized powder. For example, an agent of the invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see pharmaceutical references, supra). Such pharmaceutically acceptable carriers may include other medicinal agents, carriers, including genetic carriers, adjuvants, excipients, etc., such as human serum albumin or plasma preparations. The compositions are preferably in the form of a unit dose and will usually be administered one or more times a day.

The compositions comprising a compound of this invention will contain from about 0.1 to about 90% by weight of the active compound, and more generally from about 10% to about 30%. The compositions may contain common carriers and excipients, such as corn starch or gelatin, lactose, sucrose, microcrystalline cellulose, kaolin, mannitol, dicalcium phosphate, Sodium chloride and alginic add. The compositions may contain croscarmellose sodium, microcrystalline cellulose, corn starch, sodium starch glycolate and alginic acid.

For oral administration, the pharmaceutical compositions are in the form of, for example, a tablet, capsule, suspension or liquid. Solid formulations such as tablets and capsules are particularly useful. Sustained release or enterically coated preparations may also be devised. For pediatric and geriatric applications, suspensions, syrups and chewable tablets are especially suitable. The pharmaceutical composition is preferably made in the form of a dosage unit containing a therapeutically-effective amount of the active ingredient. Examples of such dosage units are tablets and capsules.

For therapeutic purposes, the tablets and capsules which can contain, in addition to the active ingredient, conventional carriers such as binding agents, for example, acacia gum, gelatin, methylcellulose, sodium carboxymethylcellulose, polyvinylpyrrolidone (Povidone), hydroxypropyl methylcellulose, sucrose, starch and ethylcellulose sorbitol, or tragacanth; fillers, for example, calcium phosphate, glycine, lactose, maize-starch, sorbitol, or sucrose; lubricants, for example, magnesium stearate, or other metallic stearates, stearic acid, polyethylene glycol, silicone fluid, talc, waxes, oils and silica, colloidal silica or talc; disintegrants, for example, potato starch, flavoring or coloring agents, or acceptable wetting agents.

Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Oral liquid preparations may comprise lipopeptide micelles or monomeric forms of the lipopeptide. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sortie acid.

For intravenous (IV) use, a water soluble form of the polyamine or arginase modulator can be dissolved in any of the commonly used intravenous fluids and administered by infusion. Intravenous formulations may include carriers, excipients or stabilizers including, without limitation, calcium, human serum albumin, citrate, acetate, calcium chloride, carbonate, and other salts. Intravenous fluids include, without limitation, physiological saline or Ringer's solution. Polyamine and arginase modulators, optionally coupled to other carrier molecules, may also be placed in injectors, cannulae, catheters and lines.

Formulations for parenteral administration can be in the form of aqueous or non-aqueous isotonia sterile injection solutions or suspensions. These solutions or suspensions can be prepared from sterile powders or granules having one or more of the carriers mentioned for use in the formulations for oral administration. Lipopeptide micelles may be particularly desirable for parenteral administration. The compounds can be dissolved in polyethylene glycol, propylene glycol, ethanol, corn oil, benzyl alcohol, sodium chloride, and/or various buffers. For intramuscular preparations, a sterile formulation of a polyamine or arginase modulatory agent, or a suitable soluble salt form of the compound, for example a hydrochloride salt, can be dissolved and administered in a pharmaceutical diluent such as Water-for-Injection (WFI), physiological saline or 5% glucose.

Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in microemulsions that are compatible with body tissues.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. For topical preparations, a sterile formulation of a polyamine or arginase modulatory agent or suitable salt forms thereat may be administered in a cream, ointment, spray or other topical dressing. Topical preparations may also be in the form of bandages that have been impregnated with a therapeutic composition.

For application to the eyes, nose or ears, the compounds of the present invention can be presented in liquid or semi-liquid form optionally formulated in hydrophobic or hydrophilic bases as ointments, creams, lotions, paints or powders. For rectal or vaginal administration the compounds of the present invention can be administered in the form of suppositories admixed with conventional carriers such as cocoa butter, wax or other glyceride. For aerosol preparations; a sterile formulation of the peptide or lipopeptide or salt form of the compound may be used in inhalers, such as metered dose inhalers, and nebulizers.

Alternatively, the compounds of the present invention can be in powder form for reconstitution in the appropriate pharmaceutically acceptable carrier at the time of delivery. In one embodiment, the unit dosage form of the compound can be a solution of the compound or a salt thereof in a suitable diluent in sterile, hermetically sealed ampules. The concentration of the compound in the unit dosage may vary, e.g. from about 1 percent to about 50 percent, depending on the compound used and its solubility and the dose desired by the physician. If the compositions contain dosage units, each dosage unit preferably contains from 50-500 mg of the active material. For adult human treatment, the dosage employed preferably ranges from 100 mg to 3 & per day, depending on the route and frequency of administration.

The pharmaceutical compositions of this invention may also be administered using microspheres, liposomes, other microparticulate delivery systems or controlled or sustained release formulations placed in, near, or otherwise in communication with affected tissues, the bloodstream, the cerebrospinal fluid, or other locations, including muscle, which enable the targeting of the agent to an affected location in the nervous system. The compositions of the invention can be delivered using controlled (e.g., capsules) or sustained release delivery systems (e.g., bioerodable matrices). Exemplary delayed release delivery systems for drug delivery, that are suitable for administration of the compositions of the invention are described in U.S. Pat. No. 4,452,775 (issued to Kent), U.S. Pat. No. 5,239,660 (issued to Leonard), U.S. Pat. No. 3,854,480 (issued to Zaffaroni).

Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., Biopolymers, 22, pp. 547-56 (1985)); poly(2-hydroxyethyl-methacrylate) or ethylene vinyl acetate (Langer et al., *J. Biomed. Mater. Res.*, 15, pp. 167-277 (1981); Langer, *Chem. Tech.*, 12, pp. 98-105 (1982)).

Liposomes containing polyamine and arginase modulatory agents can be prepared by well-known methods (See., e.g. DE 3,218,121; Epstein et al., *Proc. Natl. Acad. Sci. U.S.A.* 82, pp. 3688-92 (1985); Hwang et al., *Proc. Natl. Acad. Sci U.S.A.*, 77, pp. 4030-34 (1980); U.S. Pat. Nos. 4,485,045 and 4,544, 545). Ordinarily the liposomes are of the small (about 200-800 Angstroms) unilamellar type in which the lipid content is greater than about 30 mol. % cholesterol. The proportion of cholesterol is selected to control the optimal rate of agent release.

The polyamine and arginase modulatory agents of this invention may also be attached to liposomes, which may optionally contain other agents to aid in targeting or administration of the compositions to the desired treatment site. Attachment of such agents to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., *J. Cell, Biochem.* Abst. Suppl. 16E 77 (1992)).

Routes of Administration

Cells which have been engineered to express one or more polyamine or arginase modulatory agents of the invention may be used in therapeutic treatment regimes. Such engineered cells may be used to synthesize a therapeutic agent which can then be administered independently to a host. Alternatively, cells transformed, transfected, or infected with exogenous nucleic acid such as DNA or RNA that activates expression of a polyamine or arginase modulatory agent of the invention that is secreted or released from the engineered cell may be used directly as a therapeutic, e.g., by implanting such engineered cells into a host at a region which is in communication with the targeted tissue or cells in need of treatment.

Viral or non-viral gene delivery into cells which then over (or under) express a polyamine or arginase modulatory agent according to the invention may be performed in vitro or in vivo by any of a number of techniques well known to those of skill in the art. A number of such delivery methods have been shown to work with neurons. See, e.g., Cherksey et al., U.S. Pat. No. 6,210,664 (Method for gale transfer to the central nervous system involving a recombinant retroviral expression vector); Kaplitt et al., U.S. Pat. No. 6,180,613 (AAV-mediated delivery of DNA to cells of the nervous system); Hayes et al., U.S. Pat. No. 6,096,716 (Liposome-mediated transfection of central nervous system cells); Kochanek et al, U.S. Pat. No. 5,981,225 (Gene transfer vector, recombinant adenovirus particles containing same, method for producing the same and method of use of the same); Gage et al., U.S. Pat. No. 5,762,926 (Method of grafting genetically modified cells to treat defects, disease or damage to the central nervous system); WO1008192 (Herpes viral vectors for gene delivery); and CA2247912 (Genetically engineered primary oligodendrocytes for transplantation-mediated gene delivery in the central nervous system); the entire disclosures of which are incorporated herein by reference.

As shown herein, for example, neuronal cells can be infected with a viral vector which causes the infected host cells to express arginase at high levels. Arginase I, which is not normally a secreted protein, can be engineered to possess a signal peptide required for secretion of a protein from a host cell. Such signal peptides are characterized by their length (about 16-30 amino acids) and hydrophobicity and which are not highly conserved at the amino acid sequence level (see, e.g., Lodish et al., Molecular Cell Biology, 3d ed., Scientific American Books, W.H. Freeman and Company, New York, 1995, Chapter 16). Amino acid residues which function as a signal sequence for secretion in a eukaryotic cell may be engineered onto the N-terminus of a heterologous protein by any of a number of routine genetic engineering methods well known to those of skill in the art. See, e.g., Farrell et al., *Proteins*, 41, pp. 144-53 (2000) (see also http://www.healthtech.com/2001/pex); Bomgraber et al., *Protein Expr. Purif.*, 14, pp. 237-46 (1998); Collins-Racie et al., *Biotechnology*, 13, pp. 982-987 (1995); U.S. Pat. No. 5,747,662; WO00/50616; WO99/53059; and WO96/27016; each of which is incorporated herein by reference in its entirety.

Host cells which express a secreted form of arginase would be expected to elevate arginase levels in the cerebrospinal fluid (CSF) which bathes the nervous system. Such arginase would then convert arginine in the CSF to ornithine which would be taken up by other cells as arginine, by cationic amino acid transporters. Alternatively, it is possible to provide arginase, e.g., by injection, directly to the CSF. Ornithine would then be available at higher levels for polyamine synthesis through the actions of intracellular ornithine decarboxylase (ODC). Transfected cells, secreting other forms of arginase modulatory agents, may be administered to a site of neuronal injury or degeneration in a similar manner.

In addition, it is possible to target endogenous genes directly by homologous recombination techniques. Such techniques allow the skilled worker to replace or modify endogenous genes in a mammalian cell for activation, inactivation or alteration of gene coding, including intracellular targeting sequences, and non-coding (regulatory) sequences, such as transcription control sequences and other regulatory sequences which control expression levels of selected genes that modulate putrescine, polyamine or arginase activity. For homologous recombination techniques, see, e.g., U.S. Pat. Nos. 6,214,622 and 6,054,288, which are incorporated herein by reference. For polyamine regulatory sequences, see, e.g., Veress et al., *Biochem. J.*, 346, pp. 185-191 (2000); Shanti and Pegg; *Int. J. Biochem. Cell Biol.*, 31, pp. 107-122 (1999); Schantz et al., *Cancer Res.* 56, pp. 3265-3269 (1996a) and *Cancer Res.*, 56, pp. 5136-5140 (1996b).

Putrescine, derivative polyamine and arginase modulatory agents of this invention can also be delivered by spinal implantation (e.g., into the cerebrospinal fluid) of cells or other biocompatible materials engineered to release or secrete polyamine and arginase modulatory agents according to this invention. Cell secretion rates or material release rates of the agent are measured in vitro (e.g., in cell culture where applicable) and then extrapolated based on relative volumes, in vivo half-lives, and other parameters understood by those of skill in the art.

Optionally, transfected cells or biocompatible delivery materials that release polyamine and arginase modulatory agents may be encapsulated into immunoisolatory capsules or chambers and implanted into the brain or spinal cord region using available methods that are known to those of skill in the art. See, e.g.; U.S. Pat. Nos. 6,179,826, 6,083,523; 5,676,943; 5,653,975 and 5,487,739; and WO 89/04655; WO 92/19195; WO93/00127; EP 127,989; all of which are incorporated herein by reference.

Alternatively, a pump and catheter-like device may be implanted at or inserted into the site of injury to administer an agent of the invention on a timely basis and at the desired concentration, which can be selected and empirically modified by one of skill in the art. Such pharmaceutical delivery systems are well known to those of skill in the art. See, e.g., U.S. Pat. No. 4,578,057 and references cited therein; for implantable pumps, see, e.g., http://www.medtronic.com/); which are each incorporated herein by reference.

In a further aspect, this invention provides a method for treating a condition, disease or disorder associated with neuronal degeneration or lack of neuronal growth in mammals, including humans and other animals. The term "treating" is used to denote both the prevention of neuronal death and the control of axonal growth, axonal sprouting, and neural progenitor cell proliferation after the host animal has become affected. An established condition, disease or disorder may be one that is acute or chronic. The method comprises administering to the human or other animal an effective dose of a compound of this invention. An effective dose of putrescine, for example, is generally between about $10^{-6}$ and about $10^{6}$ µM/kg putrescine, putrescine-related analogs or derivatives, or pharmaceutically acceptable salts thereof. The putrescine, putrescine-related analogs or derivatives may be administered alone or as part of a combination therapy. A preferred dose is from about 0.5 to about 80 µM/kg of putrescine, putrescine-related analogs or derivatives, or pharmaceutically acceptable salts thereof. A more preferred dose is from about 1 to 10 µM/kg putrescine, putrescine-related analogs or derivatives, or a pharmaceutically acceptable salt thereof. These dosages for putrescine may be used as a starting point by one of skill in the art to determine and optimize effective dosages of other putrescine, putrescine-related analogs or derivatives, and arginase modulating agents of the invention.

In one embodiment, the invention provides a method for treating a condition, disease or disorder associated with neuronal degeneration or lack of neuronal growth in a subject with a therapeutically-effective amount of a putrescine, a putrescine-derived polyamine or arginase modulatory agent of the invention. Exemplary procedures for delivering agents to the nervous system are described, e.g., in Cherskey et al., U.S. Pat. No. 6,210,664; Kaplitt et al., U.S. Pat. No. 6,180,613; Hayes et al., U.S. Pat. No. 6,096,716; Kochanek et al, U.S. Pat. No. 5,981,225; Gage et al., U.S. Pat. No. 5,762,926; WO/008192; and CA2247912; the entire contents of which are incorporated herein by reference in their entirety.

As used herein the phrase "therapeutically-effective amount" means an amount of putrescine, a putrescine-derived polyamine or arginase modulatory agent of the invention, such that the subject shows a detectable improvement in neuronal growth or regeneration after being treated under the selected administration regime (e.g., the selected dosage levels and times of treatment). The term "treating" is defined as administering; to a subject, a therapeutically-effective amount of a compound of the invention, to prevent the occurrence of or to control or eliminate symptoms associated with a condition, disease or disorder associated with neuronal death or lack of neuronal growth. The term "subject", as described herein, is defined as a mammal or a cell in culture. In a preferred embodiment, a subject is a human or other animal patient in need of treatment.

A compound of the invention can be administered alone, or in combination with other compounds (e.g., a "cocktail"), including but not limited to other compounds of the invention. A compound of the invention may be administered as a single daily dose or in multiple doses per day. The treatment regime may require administration over extended periods of time, e.g., for several days or for from two to four weeks. The amount per administered dose or the total amount administered will depend on such factors as the nature and severity of the symptoms, the age and general health of the patient, the tolerance of the patient to the treatment program.

Utility of Agents which Block the Inhibitory Affects of Myelin on Neuronal Growth and Regeneration The discovery that increasing putrescine (and derivative polyamine) levels in a neuron (for example, by increasing neuronal arginase activity) relieves inhibition of neuronal growth by myelin, and myelin inhibitors such as MAG, has potential clinical use in the situations of nervous system injury—both of the peripheral and central nervous systems— and in particular, for CNS injury. The mammalian central nervous system does not regenerate after injury even though there are many molecules present that promote and encourage a nerve to grow. The result of such injury can be paralysis or brain damage. There are molecules present in the adult CNS that will actively prevent a nerve from regenerating. It is anticipated that if these inhibitory molecules can be blocked, then an environment permissive for nerve regeneration may be engineered and neural injury treated.

Importantly, the behavior of a neuron in the presence of the specific myelin inhibitor MAG in vitro parallels its behavior in the presence of myelin both in vitro and in vivo. While not intending to be bound by theory, this suggests that similar molecular mechanisms may be used to overcome a variety of neuronal growth inhibitors. The assay systems described herein are thus extremely useful for monitoring the effect of a variety of agents, alone or in combination, on the inhibitory effects of myelin on neuronal growth. Strategies can now be designed to look for agents which relieve inhibition and which allow neurons to grow in the presence of myelin inhibitors in general or MAG in particular. Such an agent (or combination of agents) can then be administered to damaged nerves reversing the inhibitory effects of myelin or MAG in vivo and allowing nerve regeneration to proceed.

Using the assay systems described herein, the inhibitory effects of myelin and MAG were shown to be partially or fully blocked or relieved by agents that increase putrescine and derivative polyamine levels, including agents which increase arginase activity in a neuron. These agents, or modified forms of these or other agents which can modulate the activity of putrescine, derivative polyamines or arginase in a neuron may be administered, alone or in combination, to damaged nerves to reverse the inhibitory effects of myelin or MAG in vivo and to allow regeneration to proceed.

In addition, the properties of MAG as a negative axonal guidance cue may be used to guide regenerating axons to their correct target and keep them on the correct path. For this purpose, putrescine, derivative polyamines, arginase modulatory agents, or modified forms of these or other agents which can alter (e.g., increase) polyamine levels in a neuron may be administered to the precise regions of the regenerating nervous tissue to encourage or contain growth along exact pathways.

Agents that increase putrescine and derivative polyamine levels in a neuron, including agents which increase arginase activity, and methods for using compositions comprising such an agent, will thus be useful for regulating neural growth or regeneration in the nervous system and for treating injuries or damage to nervous tissue or neurons. The compositions and methods of the invention will also be useful for treating neural degeneration associated with disorders or diseases and for treating a disease, disorder or condition associated with apoptosis, necrosis or other forms of cell death, such as amyotrophic lateral sclerosis, Alzheimer's disease, Parkinson's disease, Huntington's disease, multiple sclerosis, Creutzfeldt-Jacob disease, kuru, multiple system atrophy, amyotropic lateral sclerosis (Lou Gehrig's disease), and progressive supranuclear palsy. The compositions and methods of the invention will also be useful for treating an injury or neural abnormality associated with spinal cord injury, brain injury, aneurysms and strokes. In addition, the compositions and methods of the invention will also be useful for treating an injury or neural abnormality associated with PNS injury, viral infection (e.g., by herpes virus or HIV), encephalitis (viral or non-viral), mitochondrial disease, kuru and peripheral neuropathies.

It is also anticipated that agents which increase putrescine and derivative polyamine levels, including agents which increase arginase activity in a neuron, will be useful for treating memory and learning defects and disorders associated with neuronal death or lack of neuronal growth. There are many molecular and morphological similarities between the cAMP-dependent ability of neurotrophins and dbcAMP to overcome inhibition by MAG and myelin and the changes associated with memory and learning (Bach et al., *Proc. Natl. Acad. Sci. U.S.A.,* 96, pp. 5280-85 (1999); incorporated herein by reference). The animal model of memory acquisition is termed "long-term potentiation". Long-term potentiation is cAMP-dependent, transcription-dependent and results in sprouting of axons (Ma et al., *Nat. Neurasci.,* 2, pp. 24-30 (1999) (incorporated herein by reference)). It is therefore likely that arginase, putrescine and putrescine-derived polyamines are involved in the molecular aspects of memory and learning, as they are in neuronal regeneration by overcoming inhibition by myelin inhibitors such as MAG.

It is anticipated that in vivo, after injury, application of myelin or MAG inhibitors such as putrescine, derivative polyamines and arginase modulatory agents, or modified forms of these or other agents which can modulate the activity of putrescine, derivative polyamines or arginase in a neuron, either individually or in various combinations, will block the inhibitory effects of myelin, MAG and/or other inhibitory molecules and encourage axonal regeneration to take place. In particular, it is anticipated that arginase modulatory agents such as TGFβ, IL4, IL10 and PGE2, and trophic agents such as neurotrophins (including but not limited to BDNF, GDNF, NGF, NT3, NT4, IGF1, CNTF, galanin), EGF, PDGF, bFGF, neuroregulin (also known as aria, GGF or neu), oncostatin M and LIF1, will relieve or block inhibition of endogenous myelin or MAG on neuronal growth and thereby allow nerve regeneration.

All references cited herein are hereby incorporated by reference.

The following are examples which illustrate the methods of this invention used to identify the putrescine, derivative polyamine and arginase modulatory agents which inhibit myelin and MAG's developmentally regulated effect on neurite growth, compositions of this invention which comprise such, agents, and methods comprising the administration of those compositions. These examples should not be construed as limiting: the examples are included for the purposes of illustration only and the present invention is limited only by the claims.

In order that this invention may be more fully understood, the following examples are set forth. These examples are for the purpose of illustration only and are not to be construed as limiting the scope of the invention in any way.

Example 1

Neurite Outgrowth Assays in the Presence of MAG or Myelin

Isolation of Neurons

Neurons were isolated essentially as described in Doherty at al., *Nature,* 343, pp. 464-66 (1990); Neuron, 5, pp. 209-19 (1990); and Kleitman at al., Culturing Nerve Cells, pp. 337-78, MIT Press, Cambridge, Mass./London, England (G. Banker and K Goslin, Eds.) (1991). Briefly, for animals up to nine days of age, the cerebellum, from two animals were removed and combined in 5 ml of 0.025% trypsin in PBS, triturated, and incubated for a further 10 minutes (min.) at 37° C. Trypsinization was stopped by addition of 5 ml DMEM containing 10% fetal calf serum (FCS) and cells were centrifuged at 800 rpm for 6 min. The trypsinized cells were resuspended to a single cell suspension in 2 ml of SAT containing 2% FCS (progesterone, 20 nM; selenium, 3013M; putrescine, 100 µM; insulin, 5 µg/ml; BSA 4 mg/ml; L-thyroxine, 0.1 µg/ml; tri-iodo-thyronine, 0.08 mini) (Doherty et al., 1990). For older DRG neurons, ganglia were removed from two animals and incubated in 5 ml of Sat medium containing 0.025% trypsin and 0.15% collagenase type I (Worthington) for 30 min. at 37° C. The ganglia were triturated with a fire-polished Pasteur pipette. Trypsinization was stopped by adding 5 ml of DMEM containing 10% FCS, centrifuged at 800 rpm for 6 min, and resuspended in 2 ml of SAT (DeBellard et al., 1996). Cells were counted with a Coulter counter.

Expression of MAG by Transfected CHO Cells

Chinese hamster ovary (CHO) cells deficient in the dihydrofolate reductase (dhfr) gene (Urlaub and Chasin, *Proc. Natl, Acad, Sci.* 77, pp. 4216-20 (1980)) were transfected with a MAG-cDNA expression plasmid with the dhfr gene and the L-MAG cDNA, cells with multiple copies of dbfr were selected by growing in increasing concentrations of methotrexate, and the expression of MAG by individual transfected CHO cell lines characterized as described in Mukhopadhyay et al., Neuron, 13, pp. 757-67 (1994), which is incorporated herein by reference. The MAG-expressing transfected CHO cell line) ("CHO-MAG2") in that publication was deposited on Jun. 27, 1996 with the American Type Culture Collection (ATCC) (Rockville, Md.) according to the provisions of the Budapest Treaty, and was assigned the ATCC accession number designated: ATCC CRL-12145. All restrictions on the availability to the public of the above ATCC deposit will be irrevocably removed upon the granting of a patent on this application.

Neurite Outgrowth Assays on MAG-expressing CHO Cells And Myelin

The neurite outgrowth on myelin or on transfected CHO cells was as described (Mukhopadhyay et al., 1994; Cai et al., 1999) with the following modifications. The neurite outgrowth assay was carried out by adding $5 \times 10^4$ neurons to the immobilized myelin substrate or $2 \times 10^4$ neurons to the CHO cell monolayers. Briefly, confluent monolayers of control and MAG-expressing CHO cells were established over a 24-hour (h) period in individual chambers of an 8-well tissue culture slide (Lab-Tek). Co-cultures were established as described previously (Doherty et al., Nature, 343, pp. 464-66 (1990); Neuron, 5, pp. 209-19 (1990); Mukhopadhyay et al., Neuron, 13, pp. 757-67 (1994)) by adding approximately 5000 cerebellar and dorsal, root ganglion (DRG) neurons to the CHO monolayers. Culture medium was SATO containing 2% FCS.

Where indicated, test agents dibutyryl cAMP (dbcAMP) at 1 mM in the presence or absence of the inhibitor of transcription, 5,6-dichloro-1-b-D-ribofuranosyl-benzimidazole (DRB) at 5 µM (Zandomeni at al., 1983), were added to a culture throughout the co-culture period or monolayers were incubated with agents for one hour before adding the neuronal cell suspension and included throughout the co-culture period. Where indicated, a specific ornithine decarboxylase inhibitor, DL-a-difluoromethyl-ornithine hydrochloride (DFMO) (Danzin at al., Life Sci., 24, pp. 519-524 (1979), incorporated herein by reference), was included (1 mM) with BDNP, GDNF or dbcAMP in neuron growth assays.

All types of neuron cultures were immunostained for GAP43 as described below (see also Mukhopadhyay at al., 1994). GAP43 antibody was detected by staining with Texas Red and arginase antibody was detected with anti-biotin secondary antibody followed by Texas Red-conjugated streptavidin. About 98% of the cultures were positive for GAP43.

After periods of time as indicated, the co-cultures were fixed for 30 min with 4% paraformaldehyde and permeabilized with ice-cold methanol for 2 min. The cells were then blocked for 30 min with DMEM containing 10% FCS and incubated for 2 hrs with a rabbit polyclonal antibody against the neuronal marker GAP43 (1:4000) (provided by G. P. Wilkin; see Curtis et al., J. Neurocytology, 22, pp. 39-50 (1993); GAP 43-specific monoclonal antibodies are available from Boehringher Mannheim, Cat. No. 1379 011, clone 91E12. Cells were washed three times with PBS containing 2% BSA and then incubated for 30 min at room temperature with a biotinylated donkey anti-rabbit Ig (1:300, Amersham), washed three times, and incubated with streptavidin-conjugated Texas Red (1:300, Amersham) for 30 min. After three more washes, the slides were mounted in Permfluor (Baxter) and viewed with a Zeiss fluorescent microscope. The length of the longest neurite for each GAP43-positive neuron was determined using the Biological Detection System image analysis program (Pittsburgh).

For DRG neurons, the length of the longest neurite for each GAP43-positive neuron for the first 180-200 neurons encountered when scanning the slide in a systematic manner was determined using an Oncor image analysis program. The same effects were obtained when total processes rather than the longest neurite was measured. For adenovirus infected neurons, only those neurons that were both GAP43 and GFP-positive were measured. Neurite measurements were compared between groups using a one-way analysis of variance (ANOVA).

Alternatively, other neuron-specific antibodies such as anti-neurofilament monoclonal antibodies, which are commercially available (e.g., Boehringher Mannheim, Sigma Immunochemicals), may be used starting at dilutions recommended by the manufacturer. The appropriate species-specific, biotinylated anti-Ig secondary antibody is then selected according to the species in which the primary anti-neural antibody was generated. In addition, various vital dyes (e.g., Molecular Probes, Oregon) which stain neurites may be used in this assay in place of a fluorescent neural-specific antibody.

Example 2

Analyses of Arginase Expression in Neurons

RNA Extraction, Reverse Transcription and PCR Analysis

Cerebellar neurons were primed with neurotrophins (BDNF, GDNF) or dbcAMP according to the procedures in Example 1. RNA and protein was extracted from primed neurons. The extracted RNA was used as a template for reverse transcription and PCR amplification using primers specific for the gene encoding the enzyme arginase I ("Arg I"), an isoform of arginase abundant in liver tissue but barely detectable in other tissues.

Total RNA was isolated from $2 \times 10^6$ neurons, (some of which were treated with BDNF at 200 ng/ml or dbcAMP at 1 mM overnight) using RNeasy™ kit (Qiagen) following the manufacturers' instructions. Then cDNA was synthesized from total RNA by priming with random hexamers and adding reverse transcriptional enzyme (Stratagene) at 37° C. for 2 hr. After that, ArgI cDNA was amplified with Arg I-specific primers (see below) by polymerase chain reaction (PCR). The primers were obtained from GibcoBRL.

```
Primer: Arg-197F (Acct.# N5682H09)
5' GTC CCC AAT GAC AGC CCC 3'

Primer: Arg-700R (Acct.# N5682H10)
5' CTT TTC TTC CTT CCC AGC AG 3'
```

PCR reactions were programmed as follows: One cycle at 94° C. for 4 min, followed by 30 cycles, where each cycle consists of 94° C. for 30 sec., followed by 58° C. for 30 sec., followed by 72° C. for 1.5 min. The last cycle was at 72° C. for 5 min.

Finally, ArgI amplified cDNA samples were detected by electrophoretic separation on a 1% agarose gel and staining with ethidium bromide. The results of the PCR amplification are shown in FIG. 4.

Protein Extraction and Western Blot Analysis of Arginase Expression

Neurons were lysed, proteins were extracted and the extracted proteins (23 µg of total protein per lane) separated by SDS-polyacrylamide gel (12%) electrophoresis (SDS-PAGE) according to well-known procedures (see Ausubel et al., supra). Separated proteins were transferred to nitrocellulose membrane and immunostained with antibody to Arg I. The results are shown in FIG. 5, where the arrows indicate the position of ArgI polypeptide. Polyclonal antibodies were generated against the recombinant arginase of Cavalli at al., *Biochemistry*, 33, pp. 10652-657 (1994), which described the recombinant expression and purification of rat liver arginase I in *E. coli*. Polyclonal antibodies were generated essentially according to the procedures of Hanly et al., *ILAR Journal*, 37, pp. 141-152 (1995), incorporated herein by reference.

Example 3

Sciatic Nerve Transection and Isolation of Rat Dorsal Root Ganglia

Peripheral (sciatic) nerve transection and isolation of DRG from rats was performed essentially as described previously in Zhou, X. F. et al., *J. Neurosci.*, 16, pp. 2901-2911 (1996) (incorporated herein by reference). Left-side sciatic nerve was transected at the mid-thigh level in P18 rats (Harlan Sprague Dawley). At different times (0.5 hr, 1 hr, 4 hr, 8 hr, 18 hr, 2 days (d), 3 d and 7 d) after the injury, DRG from the injured side (I) as well as the uninjured contra-lateral side (C) were removed, and proteins were extracted and analyzed by SDS-PAGE and immunoblotting (Western blotting) using the anti-arginase I polyclonal antibody described in Example 4. (FIG. 10). Unoperated DRG neurons were analyzed in parallel as a control (U).

Example 4

Ectopic Expression of Arginase in Cerebellar Neurons

The adenovirus system exemplified herein involves a new generation of adenoviruses in which the E1 and E3 early regions have been deleted. This provides room for insertion of an expression cassette of a gene or genes up to 7.5 kB in length. (Berkner, K L, *Biotechniques*, 6, pp. 616-629 (1988); Massie, B et al., *Cytotechnology*, 28, pp. 53-64 (1998b); which are incorporated herein by reference). The adenovirus has great potential use in neurons. The virus enters the cell but cannot replicate because the essential early E1 genes are absent. Adenovirus remains epichromosomal in all known cells except eggs and therefore expression differences and other biological effects due to random integration into the host chromosome are not of concern.

We subcloned the EcoR1/Pst1 fragment of rat liver arginase cDNA into the pAdCMV-GFP adenovirus transfer vector (Berkner, supra and Massie et al., supra). This transfer vector has a CMV5 promoter and GFP as reporter gene in an IBES expression cassette for very high expression levels and easy screening of recombinant and transduction efficiency visualization (available from Qbiogene, Montreal, Canada). We verified by transient transfection and immunoblotting within arginase I antibody (Example 2) that the arginase I cDNA subcloned into the transfer vector could direct synthesis of arginase I protein. These studies confirmed that the subcloned insert was in the proper orientation. Adenoviral recombinants were generated by in vivo homologous recombination in QBI-293A cells (Qbiogene, Montreal, Canada). Insertion of DNA by homologous recombination is the most efficient way of introducing a gene into AdV because the genome is too large (36 kb) to be easily manipulated. The in vivo recombination between the two DNA molecules yields recombinant infectious viruses. The plaque purified virus is amplified on 293 cells followed by double $CsCl_2$ gradient purification and viral particle titration. An adenovirus lacking arginase I and including GFP cDNA was made to use as a control. For details on vector construction, see Berkner, K. L., Development of adenovirus vectors for the expression of heterologous genes, *Biotechniques*, 6, pp. 616-629 (1988)); and Massie, B. et al., New adenovirus vectors for protein production and gene transfer, *Cytotechnology*, 28, pp. 53-64 (1998B)).

Cerebellar neurons were infected with the Ad-GFP or Ad-GFP/ArgI. Neurons were plated at a density of $0.5$-$1.0 \times 10^6$ cells per 6 cm culture plates (Corning Glass Works, Corning, N.Y., USA). Subconfluent cells were exposed to various multiplicities of infection (MOTs) of adenoviral vectors in serum-free medium. After 4 hours, fetal bovine serum was added (final concentration, 10%; GIBCO), and the incubation continued for an additional 18 hours before assays of neurite outgrowth were performed.

Preparation of Lysates and Immunoblot Analysis

For the measurement of arginase I protein levels by immunoblot, cells were harvested and washed with ice cold PBS and then resuspended ($100 \mu l/10^7$ cells) in ice cold extraction buffer containing 50 mM Tris-HCl, pH 7.4, 150 mM NaCl, 2 mM EDTA, Triton-X 100, 1 mM phenylmethylsulfonyl fluoride (PMSF), 10 micrograms/ml leupeptin, 1 micromolar pepstatin, 1 mM N-ethylmaleimide (NEM), 2 mM Na3VO4, 20 mM sodium pyrophosphate, and 50 mM NaP). Lysates were centrifuged at 15,000 RPM at 4 degrees centigrade for 30 minutes. The clear cytosol was separated from the insoluble pellet fraction and immediately used for immunoblot. The supernatants were removed carefully and the protein concentration was quantified by the Bradford method. Lysates were mixed with boiling Laemmli's buffer (1× is 100 mM Tris-HCl, pH 6.8, 4% SDS, 200 mM dithiothreitol, 20% glycerol, 2% SDS, 0.2% bromophenol blue, 10 micrograms/ml aprotinin, 10 micrograms/ml leupeptin). The samples were boiled for 10 minutes at 100° C. and centrifuged at 15,000 rpm for 10 seconds. Approximately 30 micrograms of protein was electrophoresed under reducing conditions on 10% SDS-polyacrylamide gels and transferred to nitrocellulose membrane. Membranes were blocked in 5% skim milk in TBST (Tris, pH 7.4; 150 mM NaCl; 0.05% Tween 20) for 30 minutes at room temperature. Blots were probed with primary antibodies overnight at 4° C., followed by incubation with anti-rabbit or anti-mouse IgG conjugated with horseradish peroxidase (Bio-Rad, Hercules, Calif.) for 1 hour. Signals were detected using the ECL system (Amersham Corp, Arlington, Heights, Ill.).

Determination of Arginase Activity

Arginase activity was performed on lysates of cells that had been infected with the adenovirus-arginase I vector for 24 hours. Cultured cells were lysed in 0.1% Triton X-100 containing 2 mM Pefabloc, 2 micrograms/ml pepstatin A, and 10 micrograms/ml leupeptin. Lysates were centrifuged at 12,000×g for 10 min, and supernatants were collected for arginase activity assays. Protein concentration was determined by the bicinchoninic acid assay (Pierce).

Arginase activity in cell lysates was determined by monitoring the conversion of [guanidino-$^{14}$C] arginine to [$^{14}$C] urea, using a combination of the methods of Ruegg and Russel (Ruegg, U T and Russell, A S. A rapid and sensitive assay for arginase. *Anal. Biochem.*, 102, pp. 206-212 (1980)); and Cederbaum and Spector (Cederbaum, S D, and Spector, E B Arginase activity in fibroblasts. *Am. J. Hum. Genet.*, January 30(1), pp. 91-92 (1978)), each of which is incorporated herein by reference. Briefly, [guanidino-$^{14}$C]arginine was added to lysates for 30 minutes at 37° C., and the reaction was terminated by heating at 100° C. for 3 minutes. Jack bean urease was then added to the lysate and the urease reaction was terminated after 45 minutes by the addition of 2 N HCl. Liberated $^{14}CO_2$, trapped as $Na_2^{14}CO_3$, was quantified by scintillation counting. One unit of arginase is defined as the amount of enzyme that produces one micromole of urea per minute at 37° C. (See also arginase activity assays in, e.g., Esch et al., *J. Neurosci.*, 18, pp. 4083-4095 (1998); Wu and Meninger, *Am. J. Physiol, Heart Circ. Physiol.*, 265, pp. H1965-H1971 (1993), each of which is incorporated herein by reference).

Adenovirus-infected neurons could be distinguished by their expression of green fluorescent protein (GFP) marker. The GFP marker is visualized using standard fluorescence microscopy techniques. GFP fluoresces green when illuminated by 488 nm light. The emitted fluorescence is detected using a 505 long band pass emission filter. The fluorescence can be detected by eye or using an image intensification camera, an analog to digital converter and standard image processing software. (Current Protocols in Neuroscience, Volume 1, Crawley at al., eds, John Wiley and Sons, publisher, 1997). We viewed the cells through a fluorescent microscope with a fluorescent filter at 510 nm. After 1 hour of infection, neurons were washed and incubated with Sat media for another 24-48 hrs to recover (Doherty at al., Neuron, 5, pp 209-19 (1990); incorporated herein by reference). Neurons were then transferred to MAG-expressing or control CHO cells for neurite outgrowth and immunostaining with GAP43 (Example 1). GFP-positive neurons were distinguished from glial cells, which are also infected by adenovirus, by immunostaining with GAP43 (See FIG. 9).

Example 5

Neurite Growth Assays with CHO Cells to Test Putative Polyamine and Arginase Modulating Agents that Affect Neurite Growth Regulation by Myelin or MAG The transfected CHO cell assay described in Example 1 may be used to screen and identify agents that alter neurite growth properties of a particular neuronal cell type and age in a myelin- or MAG-dependent fashion. This assay may be used to test other putative arginase, putrescine and putrescine-derived polyamine modulatory agents by including them in the co-culture and measuring their effect in the presence and absence of cell-surface MAG or myelin, as described above (Example 1).

Example 6

Experimental Modulation of Putrescine, Putrescine-Derived Polyamines And Arginase Activity Other approaches to regulating putrescine, putrescine-derived polyamines and arginase activity are also envisioned to be effective in relieving inhibition of regeneration and repair in the nervous system. The activation or enhancement of arginase activity in neurons, for example, may be achieved in a variety of ways that will be apparent to those of skill in the ark Arginase small molecule activators will be useful according to the invention (supra) and are known to those of skill in the art. New arginase inhibitors can be readily identified using routine enzymatic or other assays for arginase biological activity. In addition, the activation or enhancement of arginase activity in neurons, for example, may be achieved by gene transfer techniques.

Methods for viral or non-viral-mediated gene transfer into neurons and glial cells of the nervous system are known to those of skill in the art. Arginase polynucleotides which are capable upon expression of elevating arginase activity in a cell of the nervous system may be transferred into such a cell directly. Arginase overexpression will raise ornithine and thus putrescine and putrescine-derived polyamine levels in the fluids which bathe the cells of the nervous system, e.g., the CSF, which can then be transported into cells in communication with those fluids. Alternatively, genes that regulate the expression of arginase in cells of the nervous system, and preferably in neuronal cells, may be used to modulate transcriptional activity of the arginase gene. Inducible and other regulated expression of arginase polynucleotides is contemplated to be within the scope of this invention using known and available transcription control sequences and expression systems for regulating heterologous genes.

Opposite biological effects from those demonstrated herein (e.g., blocking neuronal growth or regeneration) may be desirable under certain situations, such as controlled neuronal or axonal growth guidance in the presence of neuronal growth activators. Such effects may be achieved in a neuron by blocking cAMP signaling, arginase I activity or the formation of putrescine and putrescine-derived polyamines. One way to accomplish this is to inhibit protein kinase A (PKA) catalytic subunits with molecules that can bind to PKA ATP binding sites. Inhibitors that compete for ATP binding have been described and will be useful for such purposes. They include H89 (5 µM) (Chijiwa at al., *J. Biol. Chem.*, 265, pp. 5267-72 (1990)) and KT5720 (200 nM) (Kase at al., *Biochem. Biophvs. Res. Commun.* 142, pp. 436-440 (1987)); each of which is incorporated herein by reference Inhibitors of the regulatory subunit of PKA that compete to the cAMP binding site are also known. Such PKA regulatory subunit inhibitors (e.g., Rp-cAMP (20 µM)) will be useful for blocking cAMP signaling arginase I activity and the formation of putrescine and putrescine-derived polyamines in a neuron (Rothermel et al., *Biochem. J.* 251, pp. 757-62 (1988), which is incorporated herein by reference).

In addition, as described herein, DFMO (1 mM) is a non-toxic, specific, irreversible inhibitor of ornithine decarboxylase (ODC) which releases a conjugated imine that binds to ODC and thereby inhibits its catalytic activity. (Danzin et al., *Life Sci.*, 24, pp. 519-524 (1979). It is envisioned that it will be possible to direct DFMO to specific target neurons in a way that blocks ODC action and thus the pathway by which myelin inhibitors affect neuronal growth.

We claim:

1. A method for altering neural growth or regeneration, said method comprising administering, in the presence of MAG or myelin, a composition comprising arginase in vitro to cultured cerebellar neurons.

2. The method of claim 1, further comprising the step of monitoring growth of a neuron after administering the composition.

* * * * *

UNITED STATES PATENT AND TRADEMARK OFFICE
CERTIFICATE OF CORRECTION

PATENT NO. : 8,673,594 B2  
APPLICATION NO. : 12/613310  
DATED : March 18, 2014  
INVENTOR(S) : Marie T. Filbin and Rajiv R. Ratan Page 1 of 1

It is certified that error appears in the above-identified patent and that said Letters Patent is hereby corrected as shown below:

IN THE SPECIFICATION:

Column 38, Line 61  
    Now Reads: "dbfr"  
    Should Read: "dhfr"

Column 43, Line 53  
    Now Reads: "ark"  
    Should Read: "art."

Signed and Sealed this  
Second Day of September, 2014

Michelle K. Lee  
*Deputy Director of the United States Patent and Trademark Office*